US010098352B2

(12) United States Patent
Woods et al.

(10) Patent No.: US 10,098,352 B2
(45) Date of Patent: Oct. 16, 2018

(54) HONEYBEE REPELLENTS AND USES THEREOF

(71) Applicant: Inscent, Inc., Irvine, CA (US)

(72) Inventors: Daniel F. Woods, Irvine, CA (US); Spiros Dimitratos, Ontario, CA (US); Robin W. Justice, Laguna Niguel, CA (US)

(73) Assignee: Inscent, Inc., Irvine, CA (US)

( * ) Notice: Subject to any disclaimer, the term of this patent is extended or adjusted under 35 U.S.C. 154(b) by 0 days.

(21) Appl. No.: 15/225,755

(22) Filed: Aug. 1, 2016

(65) Prior Publication Data
US 2016/0330960 A1 Nov. 17, 2016

Related U.S. Application Data

(63) Continuation of application No. 14/115,800, filed as application No. PCT/US2012/036670 on May 4, 2012, now Pat. No. 9,439,434.

(60) Provisional application No. 61/482,995, filed on May 5, 2011, provisional application No. 61/495,639, filed on Jun. 10, 2011.

(51) Int. Cl.
| | | |
|---|---|---|
| *C07D 231/12* | (2006.01) |
| *A01N 43/90* | (2006.01) |
| *A01N 65/00* | (2009.01) |
| *A01N 43/10* | (2006.01) |
| *A01N 43/38* | (2006.01) |
| *A01N 43/40* | (2006.01) |
| *A01N 43/42* | (2006.01) |
| *A01N 43/60* | (2006.01) |
| *A01N 43/76* | (2006.01) |
| *A01N 43/78* | (2006.01) |
| *A01N 43/84* | (2006.01) |
| *A01N 33/20* | (2006.01) |
| *A01N 35/02* | (2006.01) |
| *A01N 35/10* | (2006.01) |
| *A01N 37/10* | (2006.01) |
| *A01N 37/28* | (2006.01) |
| *A01N 37/46* | (2006.01) |
| *A01N 43/36* | (2006.01) |
| *A01N 43/46* | (2006.01) |
| *A01N 65/36* | (2009.01) |
| *A01N 43/12* | (2006.01) |
| *A01N 43/56* | (2006.01) |
| *C07D 231/14* | (2006.01) |

(52) U.S. Cl.
CPC ............ *A01N 43/90* (2013.01); *A01N 33/20* (2013.01); *A01N 35/02* (2013.01); *A01N 35/10* (2013.01); *A01N 37/10* (2013.01); *A01N 37/28* (2013.01); *A01N 37/46* (2013.01); *A01N 43/10* (2013.01); *A01N 43/12* (2013.01); *A01N 43/36* (2013.01); *A01N 43/38* (2013.01); *A01N 43/40* (2013.01); *A01N 43/42* (2013.01); *A01N 43/46* (2013.01); *A01N 43/60* (2013.01); *A01N 43/76* (2013.01); *A01N 43/78* (2013.01); *A01N 43/84* (2013.01); *A01N 65/00* (2013.01); *A01N 65/36* (2013.01)

(58) Field of Classification Search
CPC ........ A01N 25/00; A01N 25/18; A01N 51/00; A01N 33/20; A01N 35/02; A01N 35/10; A01N 37/10; A01N 37/28; A01N 37/46; A01N 43/36
USPC ......................................................... 504/100
See application file for complete search history.

(56) References Cited

U.S. PATENT DOCUMENTS

| | | | | |
|---|---|---|---|---|
| 4,449,987 A | * | 5/1984 | Lindauer ................. | C11C 5/002 424/40 |
| 5,738,863 A | * | 4/1998 | Sackin .................... | A01N 65/28 424/405 |
| 2007/0004750 A1 | | 1/2007 | Lorsbach et al. | |

FOREIGN PATENT DOCUMENTS

DE            4012224 A1     10/1991

OTHER PUBLICATIONS

The definition of "includes", Merriam-Webster [online]. [retrieved on Nov. 26, 2017]. Retrieved from: http://www.merriam-webster.com/dictionary/include.*
Field evaluation of non-pesticide chemicals as honey bee repellents Colloques—Institut National de la Recherche Agronomique (2001), 98(Hazards of Pesticides to Bees), 159-168 Coden: Coliez; ISSN: 0293-1915.*
Atkins, et al., "Repellent Additives to Reduce Pesticide Hazards to Honey Bees," American Bee Journal, Jul. 1977, vol. 117, No. 7, pp. 438-439, 457.
Atkins, et al., "Repellent Additives to Reduce Pesticide Hazards to Honey Bees: Field Tests," Environmental Entomology, 1975, vol. 4, No. 2, pp. 207-210.

(Continued)

*Primary Examiner* — Johann R Richter
*Assistant Examiner* — Courtney A Brown
(74) *Attorney, Agent, or Firm* — UltimatEdge IP Law Group, P.C.; Dean G. Stathakis

(57) ABSTRACT

The present specification discloses honeybee repellents exhibiting repellent properties similar to 2-heptanone, compositions comprising such repellents, uses to repel a honeybee from a mammal, location, plant, structure treated of such repellents, and methods of treating a mammal, location, plant, structure by applying such repellents.

8 Claims, No Drawings
Specification includes a Sequence Listing.

(56) References Cited

OTHER PUBLICATIONS

Detzel, et al., "Attraction, Deterrence or Intoxication of Bees (*Apis mellifera*) by Plant Allelochemicals," Chemoecology, 1993, vol. 4, pp. 8-18.
Gupta, et al., "Efficacy of Ketones on the Foraging Behaviour of *Apis florea* F. in Field Conditions," Apidologie, 1987, vol. 18, No. 2, pp. 121-128.
Search Report and Opinion, EP12780063.9, dated Jul. 7, 2014.
The definition of "including," Merriam-Webster [online]. [retrieved on May 7, 2010]. Retrieved from http://www.merriam-webster.com/dictionary/include.

* cited by examiner

SEQUENCE LISTING

```
<160> NUMBER OF SEQ ID NOS: 2

<210> SEQ ID NO 1
<211> LENGTH: 142
<212> TYPE: PRT
<213> ORGANISM: Apis mellifera

<400> SEQUENCE: 1

Met Asn Thr Leu Val Thr Val Thr Cys Leu Leu Ala Ala Leu Thr Val
1               5                   10                  15

Val Arg Gly Ile Asp Gln Asp Thr Val Val Ala Lys Tyr Met Glu Tyr
            20                  25                  30

Leu Met Pro Asp Ile Met Pro Cys Ala Asp Glu Leu His Ile Ser Glu
        35                  40                  45

Asp Ile Ala Thr Asn Ile Gln Ala Ala Lys Asn Gly Ala Asp Met Ser
    50                  55                  60

Gln Leu Gly Cys Leu Lys Ala Cys Val Met Lys Arg Ile Glu Met Leu
65                  70                  75                  80

Lys Gly Thr Glu Leu Tyr Val Glu Pro Val Tyr Lys Met Ile Glu Val
                85                  90                  95

Val His Ala Gly Asn Ala Asp Asp Ile Gln Leu Val Lys Gly Ile Ala
            100                 105                 110

Asn Glu Cys Ile Glu Asn Ala Lys Gly Glu Thr Asp Glu Cys Asn Ile
        115                 120                 125

Gly Asn Lys Tyr Thr Asp Cys Tyr Ile Glu Lys Leu Phe Ser
    130                 135                 140

<210> SEQ ID NO 2
<211> LENGTH: 142
<212> TYPE: PRT
<213> ORGANISM: Apis cerana

<400> SEQUENCE: 2

Met Asn Thr Leu Val Thr Val Thr Cys Leu Leu Ala Ala Leu Thr Val
```

-continued

```
1               5                   10                  15
Val Arg Gly Ile Asp Gln Asp Thr Val Val Ala Lys Tyr Met Glu Tyr
            20                  25                  30

Leu Met Pro Asp Ile Met Pro Cys Ala Asp Glu Leu His Ile Ser Glu
        35                  40                  45

Asp Ile Ala Thr Asn Ile Gln Ala Ala Lys Asn Gly Ala Asp Met Ser
    50                  55                  60

Gln Leu Gly Cys Leu Lys Ala Cys Val Met Lys Arg Ile Glu Met Leu
65              70                  75                  80

Lys Gly Thr Glu Leu Tyr Val Glu Pro Val Tyr Lys Lys Ile Glu Val
                85                  90                  95

Val His Ala Gly Asn Ala Asp Asp Ile Gln Leu Val Lys Gly Ile Ala
                100                 105                 110

Asn Glu Cys Ile Glu Asn Ala Glu Gly Glu Thr Asp Glu Cys Asn Ile
            115                 120                 125

Gly Asn Lys Tyr Thr Asp Cys Tyr Ile Glu Lys Leu Phe Ser
            130                 135                 140
```

HONEYBEE REPELLENTS AND USES THEREOF

This continuation application claims the benefit of priority and the filing date pursuant to 35 U.S.C. 120 to U.S. patent application Ser. No. 14/115,800, filed Jan. 17, 2014, a 35 U.S.C. § 371 National Stage Filing of International Patent Application PCT/US0012/036670, filed May 4, 2012, which claims priority to U.S. Provisional Patent Application 61/495,639, filed Jun. 10, 2011, and U.S. Provisional Patent Application 61/482,995, filed May 5, 2011, each of which is hereby incorporated by reference I its entirety.

Honeybees use scent marks while foraging. When collecting nectar and/or pollen, foraging honeybees scent mark nectar-producing flower by depositing attractive pheromones to signal to other honeybees of a nearby rewarding food source. Honeybees also use a short-lived repellent scent mark that identifies exhausted and recently visited rewarding flowers not yet replenished with nectar. Subsequently visiting honeybees detect and avoid these nectar-depleted flowers. Over time, as nectar replenishes in the flower, the repellent scent mark fades until gone and the flower is eventually revisited by another foraging honeybee. It is presumed that the use of repellent scent marks increases foraging efficiency by reducing the time spent probing nectar-depleted flowers.

The repellent scent mark used by honeybees is 2-heptanone. Produced and secreted by the mandibular glands of adult worker honey bees, 2-heptanone is known as the alarm pheromone because under certain circumstances elicits aggressive behavior in honeybees when detected. Honeybees detect 2-heptanone using an olfactory pathway mediated by a specific odorant-binding protein called OBP2. By taking advantage of its properties, repellent formulation of 2-heptanone have been produced and used in agricultural settings. For example, 2-heptanone has been applied to crops in order to repel honeybees away from areas where toxic insecticides have also been applied, thereby reducing honeybee mortality and avoiding potential insecticide contamination of the colony and the hive products obtained thereof. However, such uses have had very limited success primarily because 2-heptanone is a considerably volatile compound, having an effective half-life of only a few hours. As such, 2-heptanone is impractical and cost-ineffective for agricultural uses because of the extensive efforts necessary to apply and maintain an effective amount of this repellent in the treated area.

Therefore, what are needed are more effective honeybee repellents that exhibit repellent properties similar to 2-heptanone, but are less volatile. The present specification discloses such honeybee repellents and uses and methods for such compounds. The disclosed honeybee repellents will benefit apiculture since honeybees are a crucial, domesticated species that is threatened by routine agricultural practices such as the use of insecticides.

Thus, aspects of the present specification disclose honeybee repellents exhibiting repellent properties similar to 2-heptanone, but are less volatile than 2-heptanone.

Other aspects of the present specification disclose a use of a honeybee repellent disclosed herein to repel a honeybee from a location treated with the honeybee repellent. In one embodiment, the disclosed use is a use of a honeybee repellent disclosed herein to repel a honeybee from foraging and/or collecting nectar from a flower of a plant treated with the honeybee repellent. In another embodiment, the disclosed use is a use of a honeybee repellent disclosed herein to repel a honeybee from a structure treated with the honeybee repellent.

Yet other aspects of the present specification disclose a method of treating a location by applying a honeybee repellent disclosed herein, wherein the application repels a honeybee from the treated location. In one embodiment, the disclosed method is a method of treating a plant by applying a honeybee repellent disclosed herein, wherein such application repels a honeybee from foraging and/or collecting nectar from a flower of the treated plant. In another embodiment, the disclosed method is a method of treating a structure by applying a honeybee repellent disclosed herein, wherein such application repels a honeybee from the treated structure.

DESCRIPTION

Honeybees are maintained by humans in order to harvest honey, beeswax, and other hive products produced by these insects for commercial markets. In the United States, for example, honeybees produce $270 million worth of honey, beeswax, and other hive products. Besides the economic importance of hive products, honeybees are critically necessary to pollinate many important agricultural crops produced worldwide. For example, honeybees pollinate over $14 billion worth of crops annually in the United States. As such, promoting and maintaining honeybee survival is of great economic importance.

Insecticides are widely used to increase the yields of agricultural crops and their use is one of the major factors behind the increase in agricultural productivity in the 20th century. However, there is an inherent tension between the use of insecticides on crop plants to control invading pest insects and the necessity of honeybees to pollinate these same plants and the economic importance of hive products. One commonly used method is to delay the use of insecticides until the honeybees pollination has occurred, and then apply the insecticide. However, foraging for nectar occurs throughout the growing season, and as such, foraging honeybees are still exposed to the insecticide. Furthermore, recent evidence suggests that commonly used nicotine-based insecticides like Clothianidin and Imidacloprid may be a causal factor in colony collapse disorder, a phenomenon in which worker honeybees from a colony abruptly disappear. As such, it would be extremely beneficial to develop and use compounds and methods of insect control that minimize honeybee mortality.

Although of significant value, honeybee pollination can also cause economic harm to certain agricultural crops. For example, certain seedless citrus fruits like seedless tangerines, grapefruit, and mandarin oranges are of great economic value due to consumer preference. These seedless fruits are self-pollinating. However, if honeybees cross-pollinate the crop plants with the pollen of a seeded citrus fruit, then these citrus fruits will develop seeds and become undesirable to the consumer. As such, citrus fruit growers employ insecticides in order to prevent honeybee cross-pollination. The most common insecticides used for this application are neonicotinoids like Clothianidin and Imidacloprid, which as discussed above, appears to be a causal factor in colony collapse disorder. One problem with this approach is that the nectar collected by honeybees from the flowers of citrus trees produces a flavorful and economically desirable honey. As such, beekeepers have historically kept colonies near citrus orchards. Thus, there is another inherent tension between the economic importance of hive products produced by honeybees versus the financial harm caused by honeybee pollination in certain agricultural crops like citrus trees. As such, it would be extremely beneficial to develop and use compounds and methods that could repel honeybees from crop plants where pollination is undesired without causing significant honeybee mortality.

Insect chemosensory proteins (CSPs) regulate or control crucial behaviors. The chemosensory system consists of several chemosensory protein (CSP) classes. Chemosensory protein classes that are important in the design of novel insect control products include soluble proteins found in the antennal hemolymph and the maxillary palps, such as odorant binding proteins (OBPs) and sensory appendage proteins (SAPs). OBPs and SAPs are carrier proteins that facilitate the transport of external stimuli such as odor molecules through the aqueous hemolymph of sensory appendages to the surfaces of neuronal cells. There, the protein/odorant molecule complexes bind G-protein coupled receptors (GPCRs) and initiate a signaling cascade that results in a behavioral response to the external odor or stimulus. Insects use chemosensory cues from the environment to control critical behaviors, such as feeding and mating. Thus, insect chemosensory proteins are promising targets for the discovery of novel insect control products based on manipulating insect behavior.

The present specification discloses improved honeybee repellents and uses and methods for such repellents. By exploiting the OBP2 olfactory pathway used by 2-heptanone, more effective repellent compounds have been identified and isolated. As such, the repellents disclosed herein manipulate the honeybees' chemosensory system by eliciting an avoidance response similar to the one initiated by 2-heptanone. The repellents disclosed herein are intended for agricultural, commercial, and consumer use. For example, the honeybee repellents disclosed herein are useful to repel honeybees from areas where insecticides have also been applied in order to reduce honeybee mortality and avoid insecticide contamination of honey, beeswax, and other hive products. As another non-limiting example, the honeybee repellents disclosed herein are useful to prevent unwanted pollination of plants by honeybees in crops where such pollination reduces the market value due to the resulting seeded fruits. As yet another non-limiting example, the honeybee repellents disclosed herein are useful to keep away honeybees from outdoor areas where human activities are occurring and would be disrupted by honeybee presence, such as, e.g., an outdoor activity like a sporting event or picnic. Similarly, the honeybee repellents disclosed herein are useful to keep away honeybees from man-made structures in order to prevent infestation of a colony, such as, e.g., a commercial building, a house, a shed, or other structure. Other uses of the honeybee repellents disclosed herein are discussed below and are readily apparent to a person of ordinary skill.

Aspects of the present specification disclose a honeybee repellent. As used herein, the term "honeybee repellent" is synonymous with "repellent compound" and refers to a compound that mimics a 2-heptanone-specific response. 2-Heptanone, $CH_3(CH_2)_4COCH_3$, CAS Registry No. 110-43-0, also known as methyl n-amyl ketone and methyl pentyl ketone, is a colorless, liquid with a banana-like, fruity odor. It is a volatile liquid at room temperature [d415 0.8197; b.p.$_{760}$ 151.5 OC.] and soluble in alcohol or ether and very slightly soluble in water. 2-Heptanone is available commercially.

Bees are insects of the Order Hymenoptera, Superfamily Apoidea, and comprise a group of about 20,000 species that live throughout the world. Examples of common bees are honeybees (*Apis*), bumble bees (*Bomzbus*), small carpenter bees (*Ceratina*), large carpenter bees (*Xylocopa*), paper wasps (*Polistes*), yellow jackets (*Vespula*), and baldfaced hornets (*Vespula*). At least seven species of honeybee are commonly recognized with a total of 44 subspecies and various strains, varieties, and hybrids thereof. As used herein, the term "honeybee" refers to any member of the Order Hymeoptera, Family Apidae, and includes, without limitation, *Apis* andreniformis, *Apis* cerana, *Apis* dorsata, *Apis* florae, *Apis* koschevnikovi, *Apis* laboriosa, *Apis* mellifera, *Apis* nigrocincta, *Apis* rorea, subspecies thereof, and strains, varieties, and hybrids thereof.

In one embodiment, a honeybee repellent disclosed herein substantially mimics the attractant chemosensory cues of a natural compound produced by a plant or plant part like a flower. In an aspect of this embodiment, a honeybee repellent disclosed herein substantially mimics a repellent chemosensory cue of 2-heptanone.

In aspects of this embodiment, a honeybee repellent disclosed herein has a repellent chemosensory cue that is, e.g., about 75%, about 80%, about 85%, about 90%, about 95%, about 97%, or about 100% that of the repellent chemosensory cue of 2-heptanone. In other aspects of this embodiment, a honeybee repellent disclosed herein has a repellent chemosensory cue that is, e.g., at least 75%, at least 80%, at least 85%, at least 90%, at least 95%, or at least 97% that of the repellent chemosensory cue of 2-heptanone. In other aspects of this embodiment, a honeybee repellent disclosed herein has a repellent chemosensory cue that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the repellent chemosensory of 2-heptanone.

In an embodiment, a honeybee repellent disclosed herein has a repellent chemosensory cue that is, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold that of the repellent chemosensory cue of 2-heptanone.

In an embodiment, a honeybee repellent disclosed herein has a honeybee repellency activity. In aspects of this embodiment, presence of a honeybee repellent repels honeybees by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the honeybee repellent present. In other aspects of this embodiment, presence of a honeybee repellent repels honeybees by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, as compared to not having the honeybee repellent present.

In an embodiment, a honeybee repellent disclosed herein reduces a honeybee interaction with a mammal, a plant, structure, and/or location. In aspects of this embodiment, a honeybee repellent reduces honeybee interaction with a mammal, plant, structure, and/or location by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a honeybee repellent reduces honeybee interaction with a mammal, a plant, structure, and/or location by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a honeybee repellent disclosed herein reduces an ability of a honeybee to obtain a meal and/or nectar from a plant. In aspects of this embodiment, a honeybee repellent reduces an ability of a honeybee to obtain a meal from a plant by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a honeybee repellent reduces an ability of a honeybee to obtain a meal and/or nectar from a plant by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A honeybee repellant disclosed herein may be more stable (or less volatile) than 2-heptanone. In aspects of this embodiment, a honeybee repellant disclosed herein has a half-life of, e.g., about one day, about three days, about five days, about one week, about two weeks, about three weeks, about one month, about two months, or about three months. In other aspects of this embodiment, a honeybee repellant disclosed herein has a half-life of, e.g., at least one day, at least three days, at least five days, at least one week, at least two weeks, at least three weeks, at least one month, at least two months, or at least three months. In yet other aspects of this embodiment, a honeybee repellant disclosed herein has a half-life of between, e.g., about one day to about seven days, about three days to about seven days, about five days to about seven days, about one week to about four weeks, about two weeks to about four weeks, about three weeks to about four weeks, about one month to about four months, about two months to about four months, or about three months to about four months.

A honeybee repellent may preferentially bind, without limitation, an odorant Binding Protein 2 (OBP2). OBP2, also known as ASP2, refers to a soluble, acidic protein of about 13-16 kDa that is expressed in sensory tissues of honeybees. This protein binds 2-heptanone and escorts this compound across the hydrophilic extracellular matrix to the cell surface, where odorant receptors are located. Exemplary honeybee OBP2s include, without limitation, Apis mellifera OBP2 (SEQ ID NO: 1) and Apis cerana OBP2 (SEQ ID NO: 2). For a general review see, e.g., Dani, et al., Mapping the Expression of Soluble Olfactory Proteins in the Honeybee, J. Proteome Res. 9(4): 1822-1833 (2010); Pelosi, et al., Soluble Proteins in Insect Chemical Communication, Cell. Mol. Life Sci. 63(14): 1658-1676 (2006); Calvello, et al., Expression of Odorant-Binding Proteins and Chemosensory Proteins in Some Hymenoptera, Insect Biochem. Mol. Biol. 35(4): 297-307 (2005), each of which is hereby incorporated by reference in its entirety.

A honeybee repellent disclosed herein may be characterized by it binding affinity. Binding affinity can be described by an equilibrium dissociation constant (KD), which is defined as the ratio Kd/Ka at equilibrium; where Ka is the association rate constant of the repellent compound and kd is the dissociation rate constant of the repellent compound. Binding affinity is determined by both the association and the dissociation and alone neither high association or low dissociation can ensure high affinity. The association rate constant (Ka), or on-rate constant (Kon), measures the number of binding events per unit time, or the propensity of the repellent compound and the honeybee OBP to associate reversibly into its repellent-OBP complex. The association rate constant is expressed in $M^{-1} s^{-1}$. The larger the association rate constant, the more rapidly the repellent compound binds to its honeybee OBP, or the higher the binding affinity between repellent compound and honeybee OBP. The dissociation rate constant (Kd), or off-rate constant (Koff), measures the number of dissociation events per unit time propensity of a repellent-OBP complex to separate (dissociate) reversibly into its component molecules, namely the repellent compound and the honeybee OBP. The dissociation rate constant is expressed in $s^{-1}$. The smaller the dissociation rate constant, the more tightly bound the repellent compound is to its honeybee OBP, or the higher the binding affinity between repellent compound and honeybee OBP. The equilibrium dissociation constant (KD) measures the rate at which new repellent-OBP complexes formed equals the rate at which repellent-OBP complexes dissociate at equilibrium. The equilibrium dissociation constant is expressed in M, and is defined as Koff/Kon=[L]×[R]/[L+R], where [L] is the molar concentration of the repellent compound, [R] is the molar concentration of the honeybee OBP, and [L+R] is the molar concentration of the repellent-OBP complex, where all concentrations are of such components when the system is at equilibrium. The smaller the equilibrium dissociation constant, the more tightly bound the repellent compound is to its honeybee OBP, or the higher the binding affinity between repellent compound and honeybee OBP.

In an embodiment, a honeybee repellent disclosed herein has a binding affinity that is substantially the same as the binding affinity of the natural ligand for that honeybee OBP. In aspects of this embodiment, a honeybee repellent disclosed herein has a binding affinity for a honeybee OBP that is, e.g., about 75%, about 80%, about 85%, about 90%, about 95%, about 97%, or about 100% that of the binding affinity of the natural ligand for that honeybee OBP. In other aspects of this embodiment, a honeybee repellent disclosed herein has a binding affinity for a honeybee OBP that is, e.g., at least 75%, at least 80%, at least 85%, at least 90%, at least 95%, or at least 97% that of the binding affinity of the natural ligand for that honeybee OBP. In other aspects of this embodiment, a honeybee repellent disclosed herein has a binding affinity for a honeybee OBP that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the binding affinity of the natural ligand for that honeybee OBP.

In an embodiment, the binding affinity of a honeybee repellent that binds to a honeybee OBP has a dissociation equilibrium constant that is greater than the dissociation equilibrium constant of the natural ligand for that honeybee OBP. In aspects of this embodiment, the binding affinity of a honeybee repellent that binds to a honeybee OBP has a dissociation equilibrium constant that is greater than the dissociation equilibrium constant of the natural ligand for that honeybee OBP by, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.

In another embodiment, a honeybee repellent disclosed herein binds to a honeybee OBP with binding affinity having an association rate constant of, e.g., less than $1 \times 10^5$ $M^{-1}$ $s^{-1}$, less than $1 \times 10^6$ $M^{-1}$ $s^{-1}$, less than $1 \times 10^7$ $M^{-1}$ $s^{-1}$, or less than $1 \times 10^8$ $M^{-1}$ $s^{-1}$. In another embodiment, a honeybee repellent disclosed herein binds to a honeybee OBP with binding affinity having an association rate constant of, e.g., more than $1 \times 10^5$ $M^{-1}$ $s^{-1}$, more than $1 \times 10^6$ $M^{-1}$ $s^{-1}$, more than $1 \times 10^7$ $M^{-1}$ $s^{-1}$, or more than $1 \times 10^8 M^{-1}$ $s^{-1}$. In another embodiment, a honeybee repellent disclosed herein binds to a honeybee OBP with binding affinity having an association rate constant between $1 \times 10^5$ $M^{-1}$ $s^{-1}$ to $1 \times 10^8$ $M^{-1}$ $s^{-1}$, $1 \times 10^6$ $M^{-1}$ $s^{-1}$ to $1 \times 10^8$ $M^{-1}$ $s^{-1}$, $1 \times 10$ $M^{-1}$ $s^{-1}$ to $1 \times 10^7$ $M^{-1}$ $s^{-1}$, or $1 \times 10^6$ $M^{-1}$ $s^{-1}$ to $1 \times 10^7$ $M^{-1}$ $s^{-1}$.

In another embodiment, a honeybee repellent disclosed herein binds to a honeybee OBP with binding affinity having a disassociation rate constant of less than $1 \times 10^{-3}$ $s^{-1}$, less than $1 \times 10^{-4}$ $s^{-1}$, or less than $1 \times 10^{-5}$ $s^{-1}$. In another embodiment, a honeybee repellent disclosed herein binds to a honeybee OBP with binding affinity having a disassociation rate constant of, e.g., less than $1.0 \times 10^{-4}$ $s^{-1}$, less than $2.0 \times 10^{-4}$ $s^{-1}$, less than $3.0 \times 10^{-4}$ $s^{-1}$, less than $4.0 \times 10^{-4}$ $s^{-1}$, less than $5.0 \times 10^{-4}$ $s^{-1}$, less than $6.0 \times 10^{-4}$ $s^{-1}$, less than $7.0 \times 10^{-4}$ $s^{-1}$, less than $8.0 \times 10^{-4}$ $s^{-1}$, or less than $9.0 \times 10^{-4}$ $s^{-1}$. In another embodiment, a honeybee repellent disclosed herein binds to a honeybee OBP with binding affinity having a disassociation rate constant of, e.g., more than $1 \times 10^{-3}$ $s^{-1}$, more than $1 \times 10^{-4}$ $s^{-1}$, or more than $1 \times 10^{-5}$ $s^{-1}$. In another embodiment, a honeybee repellent disclosed herein binds to a honeybee OBP with binding affinity having a disassociation rate constant of, e.g., more than $1.0 \times 10^{-4}$ $s^{-1}$, more than $2.0 \times 10^{-4}$ $s^{-1}$, more than $3.0 \times 10^{-4}$ $s^{-1}$, more than $4.0 \times 10^{-4}$ $s^{-1}$, more than $5.0 \times 10^{-4}$ $s^{-1}$, more than $6.0 \times 10^{-4}$ $s^{-1}$, more than $7.0 \times 10^{-4}$ $s^{-1}$, more than $8.0 \times 10^{-4}$ $s^{-1}$, or more than $9.0 \times 10^{-4}$ $s^{-1}$.

In another embodiment, a honeybee repellent disclosed herein binds to a honeybee OBP with binding affinity having an equilibrium disassociation constant of less than 0.500 nM. In aspects of this embodiment, a honeybee repellent disclosed herein binds to a honeybee OBP with binding affinity having an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, a honeybee repellent disclosed herein binds to a honeybee OBP with binding affinity having an equilibrium disassociation constant of more than 0.500 nM. In aspects of this embodiment, a honeybee repellent disclosed herein binds to a honeybee OBP with binding affinity having an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In another embodiment, a honeybee repellent disclosed herein has a binding affinity that is substantially the same as the binding affinity of 2-heptanone for that honeybee OBP. In aspects of this embodiment, a honeybee repellent disclosed herein has a binding affinity for a honeybee OBP that is, e.g., about 75%, about 80%, about 85%, about 90%, about 95%, about 97%, or about 100% that of the binding affinity of 2-heptanone for that honeybee OBP. In other aspects of this embodiment, a honeybee repellent disclosed herein has a binding affinity for a honeybee OBP that is, e.g., at least 75%, at least 80%, at least 85%, at least 90%, at least 95%, or at least 97% that of the binding affinity of 2-heptanone for that honeybee OBP. In other aspects of this embodiment, a honeybee repellent disclosed herein has a binding affinity for a honeybee OBP that is between, e.g., about 75% to about 97%, about 80% to about 97%, about 85% to about 97%, about 90% to about 97%, about 75% to about 100%, about 80% to about 100%, about 85% to about 100%, or about 90% to about 100% that of the binding affinity of (R)-(+)-Limonene for that honeybee OBP.

In an embodiment, the binding affinity of a honeybee repellent that binds to a honeybee OBP has a dissociation equilibrium constant that is greater than the dissociation equilibrium constant of 2-heptanone for that honeybee OBP by, e.g., at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.

Unless otherwise indicated, when a compound or chemical structural feature, such as aryl, phenyl, or a compound named or depicted herein, is referred to as being "optionally substituted," it includes a feature that has no substituents (i.e. be unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

In some embodiments, any substituent may independently be $C_{1-5}$ alkyl, such as $CH_3$, $C_2H_5$, $C_3H_7$, $C_4H_9$, $C_5H_{11}$, cyclopropyl, cyclobutyl, cyclopentyl, etc.; $C_{1-4}$—O-alkyl, such as —O—$CH_3$, —O—$C_2H_5$, —O—$C_3H_7$, —O-cyclopropyl, etc.; $C_{2-4}$ alkenyl, such as —$CH_2$—CH=$CH_2$; —O—$CH_2$CH=$CH_2$; ester functional groups, such as $C_{1-4}$—$CO_2$-alkyl (e.g. —$CO_2CH_3$, —$CO_2C_2H_5$, —$CO_2C_3H_7$, etc.), $C_{1-4}$ acyloxy, (e.g. —$OCOCH_3$, —$OCOC_2H_5$, —$OCOC_3H_7$, etc.), —$CO_2$—$CF_3$, etc.; halo, such as F, Cl, Br, I, etc.; $NO_2$; =O; =S; —OH; amino, such as $C_{1-12}$ amino including $NH_2$, $NHCH_3$, $N(CH_3)_2$, $N(C_2H_5)_2$, $NH(C_3H_7)$, etc.; amide functional groups, such as $C_{1-12}$ amide groups including —$CONH_2$, $CONH(CH_3)$, $CON(CH_3)_2$, $CON(C_2H_5)_2$, —$NCOC_4H_9$, etc.; —C=N—OH; —C=N—$CH_3$; $C_{1-4}$ acyl, such as COH, $COCH_3$, $COC_2H_5$, etc.; $COCF_3$; —$NCOC_4H_9$; or two substituents may together be —$CH_2$—, —$C_2H_4$—, —$C_3H_6$—, —O—$CH_2$—, —O—$C_2H_4$—, —O—$C_3H_6$—, —$CH_2$—O—, —$C_2H_4$—O—, —$C_3H_6$—O—, —O—$CH_2$—O—, —O—$C_2H_4$—O—, or —O—$C_3H_6$—O—.

For convenience, the term "molecular weight" is used with respect to a moiety or part of a molecule to indicate the sum of the atomic masses of the atoms in the moiety or part of a molecule, even though it may not be a complete molecule.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_3$-10 branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

Unless otherwise indicated, any reference to a compound herein by structure, name, or any other means, includes pharmaceutically acceptable salts, such as sodium, potassium, and ammonium salts; alternate solid forms, such as polymorphs, solvates, hydrates, etc.; tautomers; or any other chemical species that may rapidly convert to a compound described herein under conditions in which the compounds are used as described herein.

Thus, in one embodiment, a honeybee repellent is a compound having a structure of formula I

wherein $X^1$ and $X^2$ are each independently selected from CH, N and O; $R^1$ and $R^2$ are each independently selected from H, $C_{1-6}$ alkyl, $C_{2-6}$ alkenyl, $C_{2-6}$ alkynyl, optionally substituted aryl, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, optionally substituted cyclic heteroalkyl, optionally substituted cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, or isoquinoline, with the proviso that if $X^1$ is O, then $R^1$ is not present, or if $X^2$ is O, then $R^2$ is not present In an aspect of this embodiment, a compound of formula I disclosed herein has a structure of formula Ia

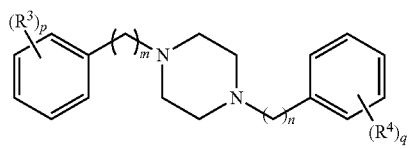

wherein $R^3$ and $R^4$ are each independently H, $C_{1-6}$ alkyl, $OC_{1-6}$ alkyl, $CO_2C_{1-6}$ alkyl, phenoxymethanol, halogen, $NO_2$, $SO_2$ or when two of $R^3$ or $R^4$ are taken together form a cyclic group including, but not limited to, methylene dioxo, benzo, morpholino, piperidinyl, dioxanyl, pyranyl, optionally substituted heteroaryl, furanyl, thiophene, pyrrole, thiazole, isothiazole, imidazole, oxazole, isoxazole, pyridinyl, pyrimidinyl or piperazine; m is 0, 1 or 2; n is 0, 1 or 2; p is 0 to 5; and q is 0 to 5.

In another aspect of this embodiment, a compound of formula I disclosed herein is

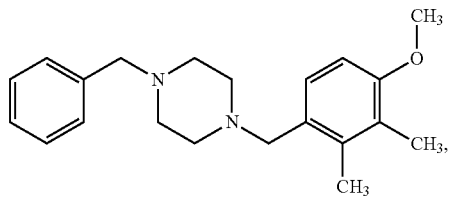

1-benzyl-4-(4-methoxy-2,3-dimethylbenzyl)piperazine

-continued

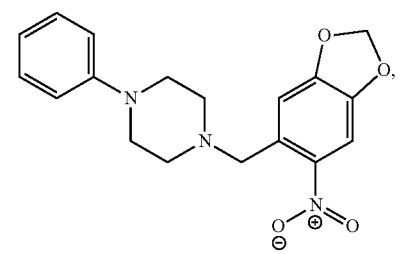

1-[(6-nitro-1,3-benzodioxol-5-yl)methyl]-
4-phenylpiperazine

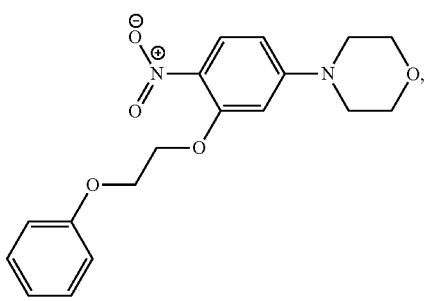

4-[4-nitro-3-(2-phenoxyethoxy)phenyl]morpholine

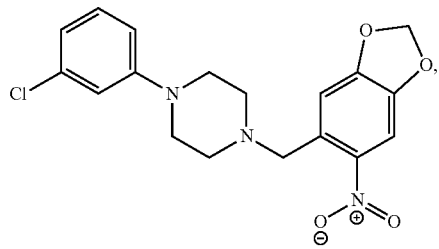

1-(3-chlorophenyl)-4-[(6-nitro-1,3-benzodioxol-
5-yl)methyl]-piperazine

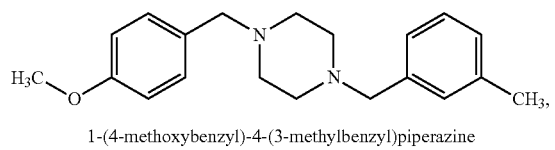

1-(4-methoxybenzyl)-4-(3-methylbenzyl)piperazine

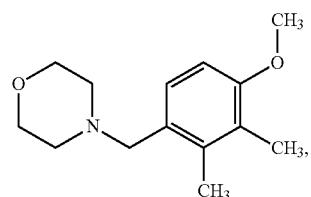

4-(4-methoxy-2,3-
dimethylbenzyl)morpholine

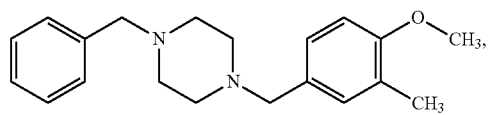

1-benzyl-4-(4-methoxy-3-methylbenzyl)piperazine

-continued

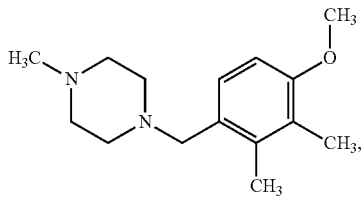

1-(4-methoxy-2,3-dimethylbenzyl)-4-
methyl piperazine

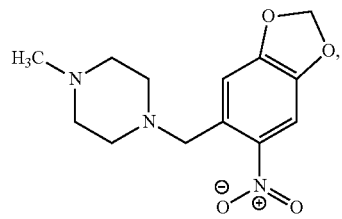

1-(4-methoxy-2,3-dimethylbenzyl)-4-
methylpiperazine

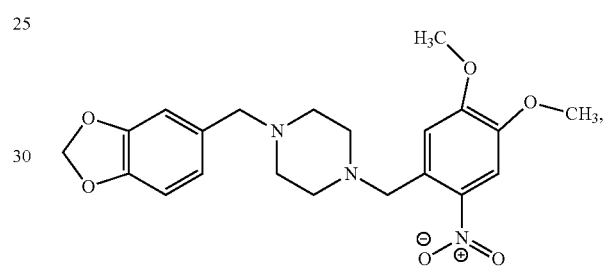

1-(1,3-benzodioxol-5-ylmethyl)-4-(4,5-dimethoxy-2-nitrobenzyl)piperazine

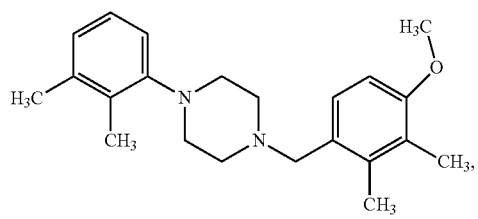

1-(2,3-dimethylphenyl)-4-(4-dimethylbenzyl)piperazine

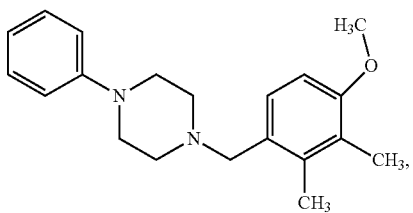

1-(4-methoxy-2,3-dimethylbenzyl)-
4-phenylpiperazine

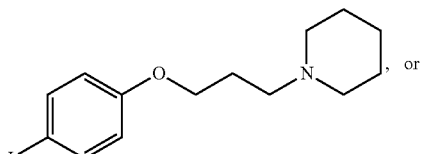, or

1-[3-(4-iodophenoxy)propyl]piperidine

-continued

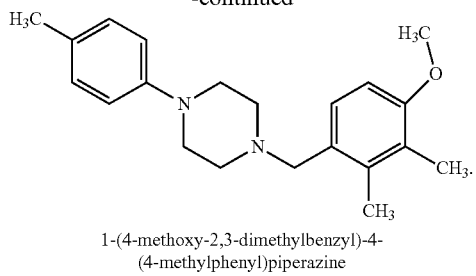

1-(4-methoxy-2,3-dimethylbenzyl)-4-(4-methylphenyl)piperazine

In another embodiment, a honeybee repellent is a compound having a structure of formula II

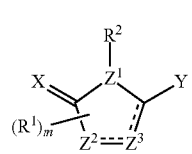

wherein X is O or S; Y is H, $C_{1-6}$ alkyl, optionally substituted aryl, =O, or =S; $Z^1$, $Z^2$, and $Z^3$ are each independently selected from N, NH, C, CH, $CH_2$, O, or S; each $R^1$ is independently selected from H, $C_{1-6}$ alkyl, $C_{2-6}$ alkenyl, $C_{2-6}$ alkynyl, optionally substituted benzylidine, optionally substituted alkylaryl, optionally substituted arylalkyl, alkoxy, optionally substituted aryloxy, optionally substituted arylalkoxy, optionally substituted alkoxyalkylaryl optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline or when two of $R^1$ are taken together form an optionally substituted cyclic group including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine; if $Z^1$ is O or S, then $R^2$ is absent, otherwise $R^2$ is H, OH, $C_{1-6}$ alkyl, optionally substituted aryl; a dashed line represents the presence or absence of a double bond; and m is 0 to 2.

In an aspect of this embodiment, a compound of formula II disclosed herein has a structure of formula IIa

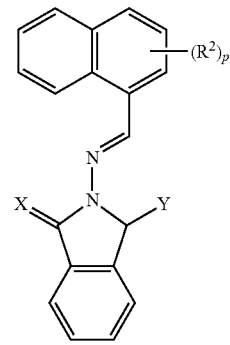

wherein $R^2$ is independently H, OH, $C_{1-6}$ alkyl, $OC_{1-6}$ alkyl, $CO_2C_{1-6}$ alkyl, halogen, $NO_2$, or $SO_2$; and p is 0 to 8.

In another aspect of this embodiment, a compound of formula II or formula IIa disclosed herein is

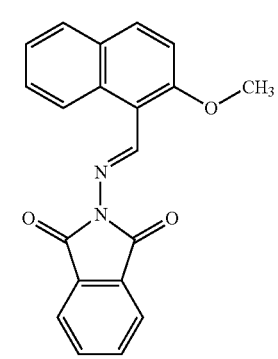

2-{[(2-methoxy-1-naphthyl)methylene]ene]amino}-1H-isoidole-1,3(2H)-dione or

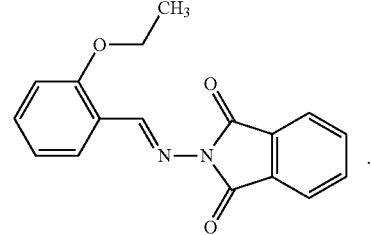

2-[(2-ethoxybenzylidene)amino]-1H-isoindole-1,3(2H)-dione

In yet another aspect of this embodiment, a compound of formula II disclosed herein has a structure of formula IIb

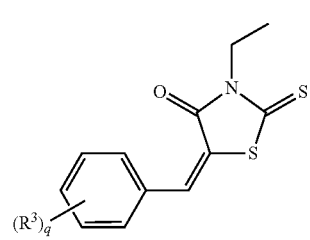

wherein each $R^3$ is independently H, OH, $C_{1-6}$ alkyl, $OC_{1-6}$ alkyl, $CO_2C_{1-6}$ alkyl, halogen, $NO_2$, or $SO_2$; and q is 0 to 5.

In yet another aspect of this embodiment, a compound of formula II or formula IIb disclosed herein is

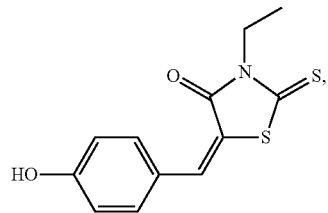

3-ethyl-5-(4-hydroxybenzylidene)-2-
thioxo-1,3-thiazolidin-4-one

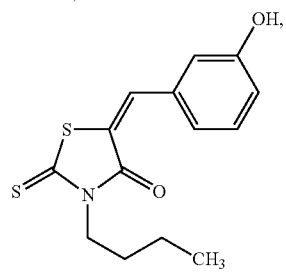

3-butyl-5-(3-hydroxybenzylidene)-2-
thioxo-1,3-thiazolidin-4-one

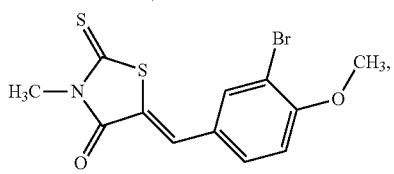 or 5-(3-bromo-4-methoxybenzylidene)-3-methyl-2-
thioxo-1,3-thiazolidin-4-one

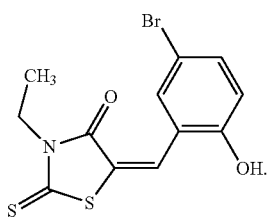

5-(5-bromo-2-
hydroxybenzylidene)-
3-ethyl-2-thioxo-
1,3-thiazolidin-4-one

In still another aspect of this embodiment, a compound of formula II disclosed herein has a structure of formula IIc

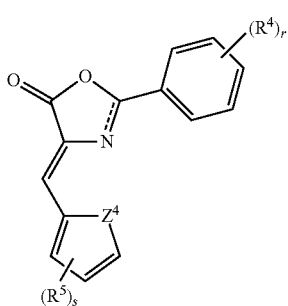

IIc wherein $R^4$ and $R^5$ are each independently H, OH, $C_{1-6}$ alkyl, $OC_{1-6}$ alkyl, $CO_2C_{1-6}$ alkyl, halogen, $NO_2$, or $SO_2$; $Z^4$ is O, NH, or S; r is 0 to 5; and s is 0 to 3.

In still another aspect of this embodiment, a compound of formula II or formula IIc disclosed herein is

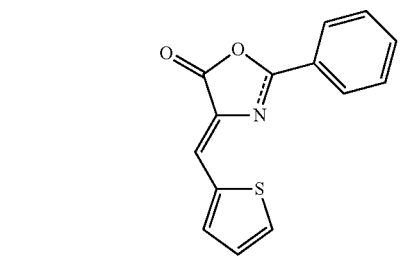

2-phenyl-4-(2-thienylmethylene)-1,3-oxazol-5(4H)-one

In yet another aspect of this embodiment, a compound of formula II disclosed herein has a structure of formula IId

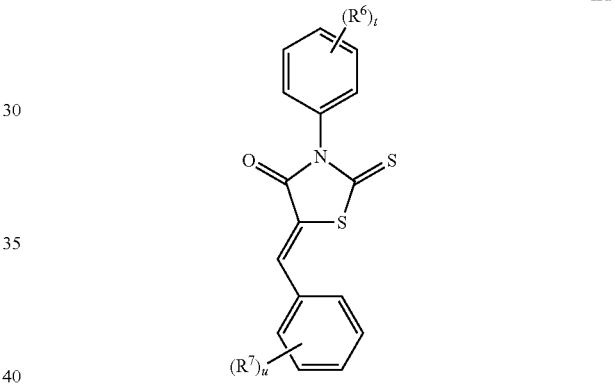

IId wherein $R^6$ and $R^7$ are each independently H, OH, $C_{1-6}$ alkyl, $OC_{1-6}$ alkyl, $CO_2C_{1-6}$ alkyl, halogen, $NO_2$, or $SO_2$; t is 0 to 5; and u is 0 to 5.

In yet another aspect of this embodiment, a compound of formula II or formula IId disclosed herein is

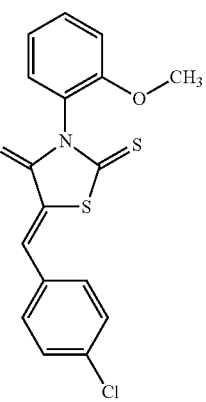

5-(4-chlorobenzylidene)-3-(2-methoxyphenyl)-2-
thioxo-1,3-thiazolidin-4-one

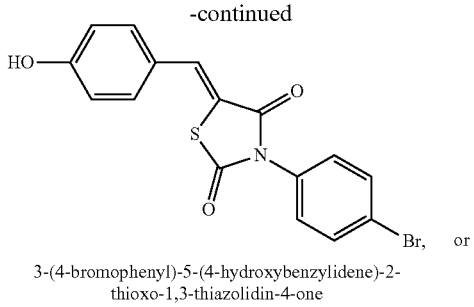

3-(4-bromophenyl)-5-(4-hydroxybenzylidene)-2-thioxo-1,3-thiazolidin-4-one

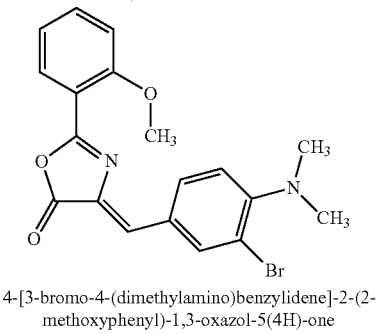

4-[3-bromo-4-(dimethylamino)benzylidene]-2-(2-methoxyphenyl)-1,3-oxazol-5(4H)-one In yet another embodiment, a honeybee repellent is a compound having a structure of formula III

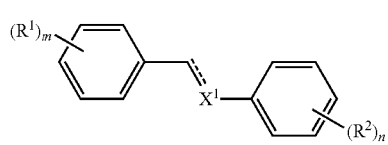

III wherein $X^1$ is O, N or S; $R^1$ and $R^2$ are each independently selected from H, $C_{1-6}$ alkyl, $C_{2-6}$ alkenyl, $C_{2-6}$ alkynyl, optionally substituted aryl, optionally substituted alkylaryl, optionally substituted arylalkyl, alkoxy, optionally substituted aryloxy, optionally substituted arylalkoxy, optionally substituted alkoxyalkylaryl optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, or isoquinoline; m is 0 to 5; and n is 0 to 5.

In an aspect of this embodiment, a compound of formula III disclosed herein is

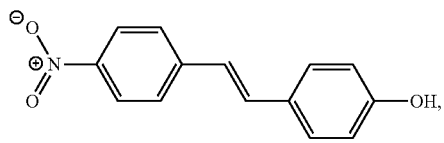

4-[2-(4-nitrophenyl)vinyl]phenol

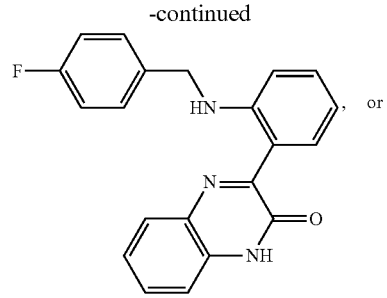

3-{2-[(fluorobenzyl)amino]phenyl}-2(1H)-quinoxalinone

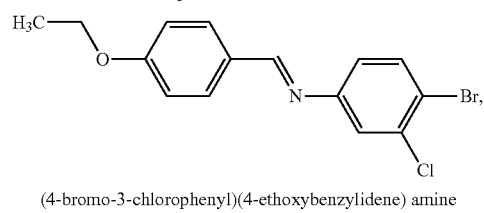

(4-bromo-3-chlorophenyl)(4-ethoxybenzylidene) amine

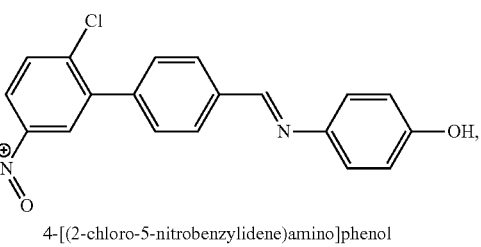

4-[(2-chloro-5-nitrobenzylidene)amino]phenol

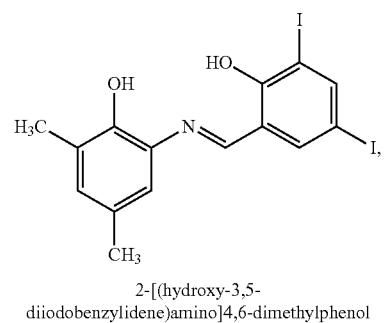

2-[(hydroxy-3,5-diiodobenzylidene)amino]4,6-dimethylphenol

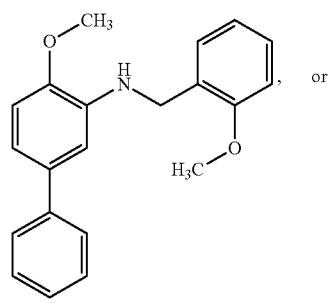

(2-methoxybenzyl)(4-methoxy-3-biphenyl)amine

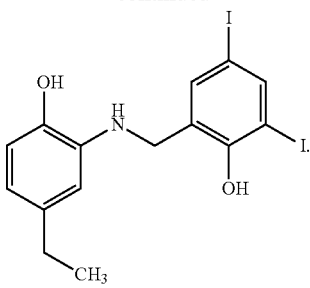

2-{[(5-ethyl-2-hydroxyphenyl)imino]methyl}-4,6-diiodophenol

In still another embodiment, a honeybee repellent is a compound having a structure of formula IV

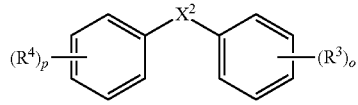

wherein $X^2$ is O, N or S; $R^3$ and $R^4$ are each independently selected from H, $C_{1-6}$ alkyl, $C_{2-6}$ alkenyl, $C_{2-6}$ alkynyl, optionally substituted alkylaryl, optionally substituted arylalkyl, alkoxy, optionally substituted aryloxy, optionally substituted arylalkoxy, optionally substituted alkoxyalkylaryl optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, C=N—OH, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, or isoquinoline; o is 0 to 5; and p is 0 to 5.

In an aspect of this embodiment, a compound of formula IV disclosed herein is

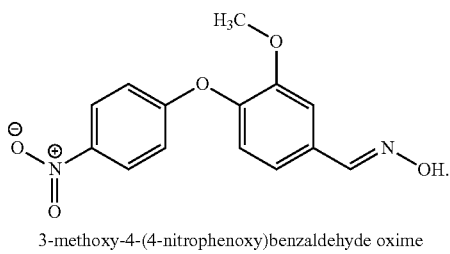 [SMILES: COc1cc(/C=N/O)ccc1Oc1ccc([N+](=O)[O-])cc1]

3-methoxy-4-(4-nitrophenoxy)benzaldehyde oxime

In a further embodiment, a honeybee repellent is a compound having a structure of formula V

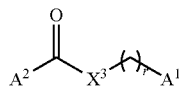

wherein $X^3$ is O, NH or S; $A^1$ and $A^2$ are each independently selected from optionally substituted phenyl, optionally substituted morpholino, optionally substituted piperidinyl, optionally substituted dioxanyl, optionally substituted pyranyl, optionally substituted heteroaryl, optionally substituted furanyl, optionally substituted thiophenyl, optionally substituted tetrazole, optionally substituted thiazole, optionally substituted isothiazole, optionally substituted imidazole, optionally substituted thiadiazole, optionally substituted thiadiazole S-oxide, optionally substituted thiadiazole optionally substituted S,S-dioxide, optionally substituted sulfonylamidine, optionally substituted sulfonylguanidine, optionally substituted sulfamoylamidine, optionally substituted sulfamoylguanidine, optionally substituted pyrazole, optionally substituted oxazole, optionally substituted isoxazole, optionally substituted pyridinyl, optionally substituted pyrimidinyl, optionally substituted piperazine, optionally substituted quinoline, optionally substituted dihydroquinoline, and optionally substituted isoquinoline; and r is 0 to 5.

In an aspect of this embodiment, a compound of formula II disclosed herein has a structure of formula Va

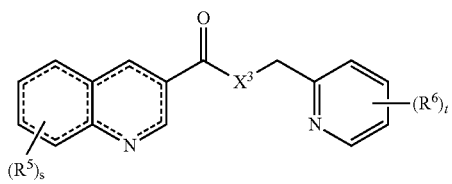

wherein a dotted line represent the presence or absence of a double bond; $R^5$ and $R^6$ are each independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; s is 0 to 9; and t is 0 to 5.

In an aspect of this embodiment, a compound of formula V or formula Va disclosed herein is

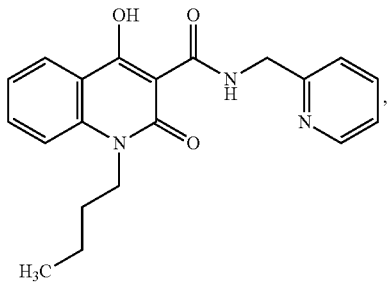

1-butyl-4-hydroxy-2-oxo-N-(2-pyridinylmethyl)-
1,2-dihydro-3-quinolinecarboxamide

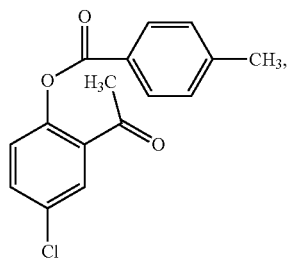

2-acetyl-4-chloroephenyl 4-
methylbenzoate

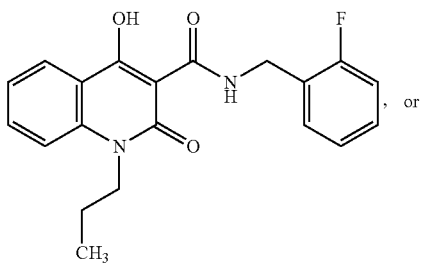, or

N-(2-fluorobenzyl)-4-hydroxy-2-oxo-1-propyl-
1,2-dihydro-3-quinolinecarboxamide

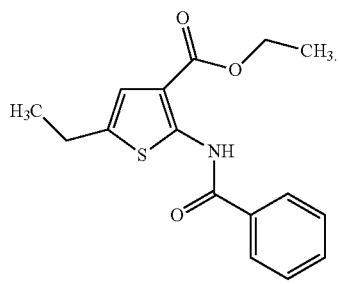

ethyl 2-(benzoylamino)-5-ethyl-3-
thiophenecarboxylate

In another embodiment, a honeybee repellent is a compound having a structure of formula VI

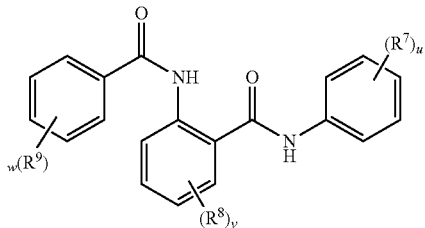

wherein $R^7$, $R^8$ and $R^9$ are each independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; u is 0 to 5; v is 0 to 5; and w is 0 to 5.

In an aspect of this embodiment, a compound of formula VI disclosed herein is

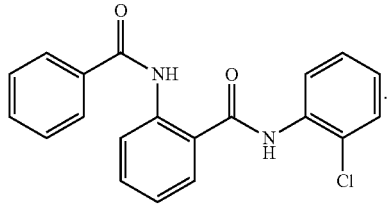

2-(benzoylamino)-N-(2-chlorophenyl)benzamide

In yet another embodiment, a honeybee repellent is a compound having a structure of formula VII

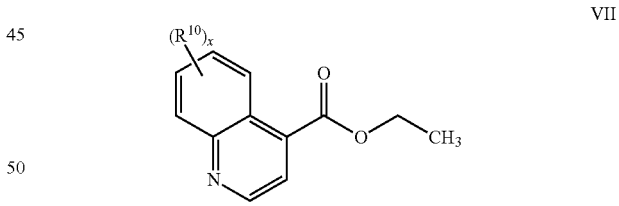

wherein each $R^{10}$ is independently selected from H, $C_{1-6}$ alkyl, $C_{2-6}$ alkenyl, $C_{2-6}$ alkynyl, =S, =O, optionally substituted phenyl, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; and x is 0 to 9.

In an aspect of this embodiment, a compound of formula VII disclosed herein is

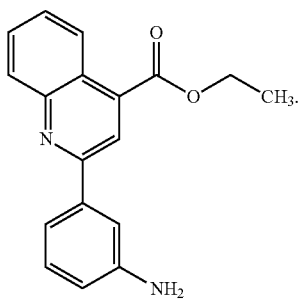

ethyl 2-(3-aminophenyl)-
4-quinolinecarboxylate

In still another embodiment, a honeybee repellent is a compound having a structure of formula VIII

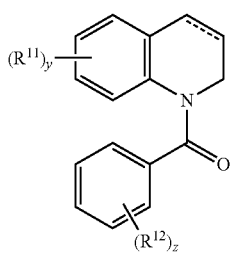

VIII wherein $R^{11}$ and $R^{12}$ are each independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; the dashed line represents the presence or absence of a double bond; y is 0 to 9; and z is 0 to 5.

In an aspect of this embodiment, a compound of formula VIII disclosed herein is

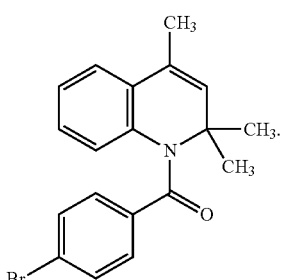

1-(4-bromobenzoyl)-2,2,4-trimethyl-
1,2-dihydroquinoline

In a further embodiment, a honeybee repellent is a compound having a structure of formula IX

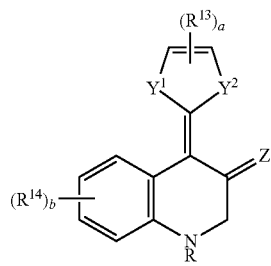

IX wherein R is H, OH, halogen, $C_{1-6}$ alkyl; $R^{13}$ and $R^{14}$ are each independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; $Y^1$ and $Y^2$ are each independently selected from O, S, NH, or $CH_2$; Z is O or S; a is 0 to 5; and b is 0 to 9.

In an aspect of this embodiment, a compound of formula IX disclosed herein is

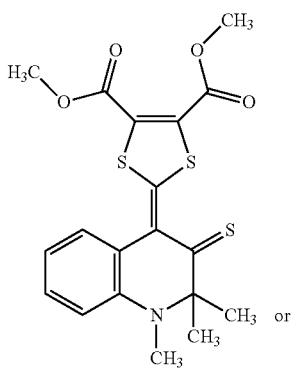

dimethyl 2-(1,2,2-trimethyl-3-
thioxo-2,3-dihydro-4(1H)-
quinolinylidene)-1,3-dithiole-
4,5-dicarboxylate

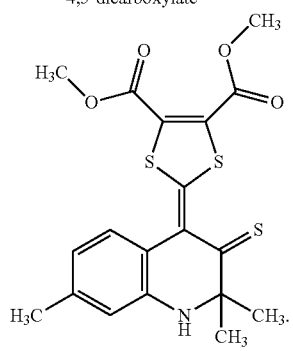

dimethyl 2-(2,2,7-trimethyl-3-thioxo-
2,3-dihydro-4(1H)-quinolinylidene)-
1,3-dithiole-4,5-dicarboxylate In another embodiment, a honeybee repellent is a compound having a structure of formula X

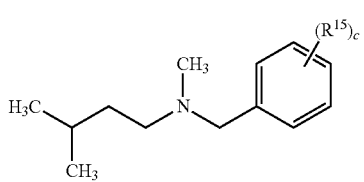

wherein each $R^{15}$ is independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; and c is 0 to 5.

In an aspect of this embodiment, a compound of formula X disclosed herein is

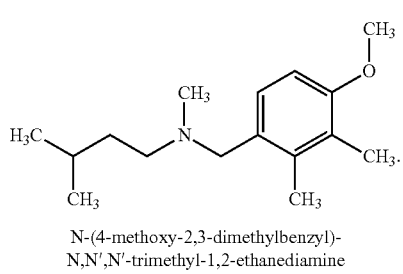 [SMILES: COc1ccc(CN(C)CCC(C)C)c(C)c1C]

N-(4-methoxy-2,3-dimethylbenzyl)-
N,N′,N′-trimethyl-1,2-ethanediamine

In yet another embodiment, a honeybee repellent is a compound having a structure of formula XI

XI

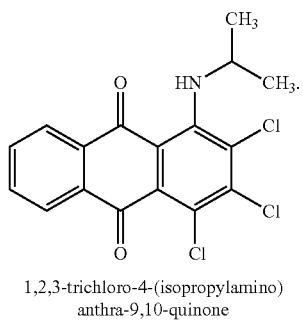

wherein each $R^{16}$ is independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; and d is 0 to 9.

In an aspect of this embodiment, a compound of formula XI disclosed herein is

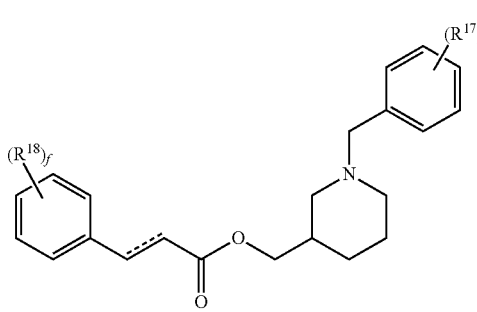

1,2,3-trichloro-4-(isopropylamino)
anthra-9,10-quinone

In yet another embodiment, a honeybee repellent is a compound having a structure of formula XII

XII

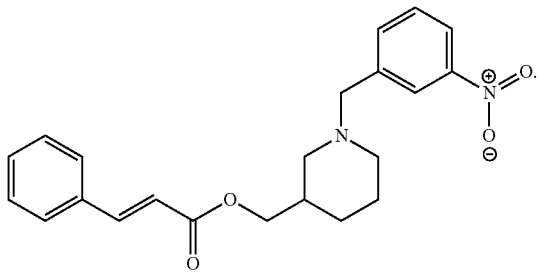

wherein $R^{17}$ and $R^{18}$ are each independently selected from H, $C_{1-6}$ alkyl, $C_{2-6}$ alkenyl, $C_{2-6}$ alkynyl, =S, =O, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino; a dashed line represent the presence or absence of a double bond; e is 0 to 5; and f is 0 to 5.

In an aspect of this embodiment, a compound of formula XII disclosed herein is

[1-(3-nitrobenzyl)-3-piperidinyl]methyl 3-phenylacrylate

In still another embodiment, a honeybee repellent is a compound having a structure of formula XIII

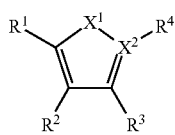

XIII wherein $X^1$ and $X^2$ are each independently selected from O, N or S; and $R^1$, $R^2$, $R^3$, and $R^4$ are each independently selected from H, $C_{1-6}$ alkyl, $C_{2-6}$ alkenyl, $C_{2-6}$ alkynyl, optionally substituted alkylaryl, optionally substituted arylalkyl, alkoxy, optionally substituted aryloxy, optionally substituted arylalkoxy, optionally substituted alkoxyalkylaryl, alkylamino, aminoalkyl, dialkylamino, optionally substituted arylamino, optionally substituted aminoaryl, heteroalkyl, optionally substituted heteroaryl, optionally substituted heteroarylalkyl, cyclic heteroalkyl, cyclic heteroalkylalkyl, acyl, optionally substituted benzoyl, optionally substituted 2-benzoylethenyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, optionally substituted heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline or when $R^3$ and $R^4$ are taken together form a cyclic group including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine and substituted derivatives thereof.

In an aspect of this embodiment, a compound of formula XIII disclosed herein has a structure of formula XIIIa

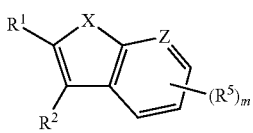

XIIIa wherein each $R^5$ is independently H, OH, $C_{1-6}$ alkyl, $OC_{1-6}$ alkyl, $CO_2C_{1-6}$ alkyl, halogen, $NO_2$, or $SO_2$; Z is C or N; and m is 0 to 5.

In an aspect of this embodiment, a compound of formula XIII or formula XIIIa disclosed herein is

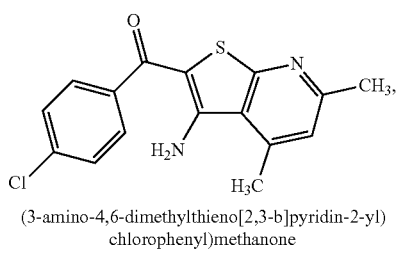

(3-amino-4,6-dimethylthieno[2,3-b]pyridin-2-yl)
chlorophenyl)methanone

-continued

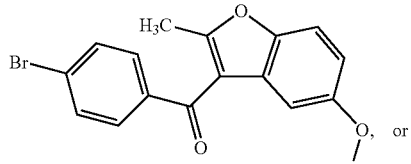

(4-(4-bromophenyl)(5-methoxy-2-methyl-1-
benzofuran-3-yl)methanone

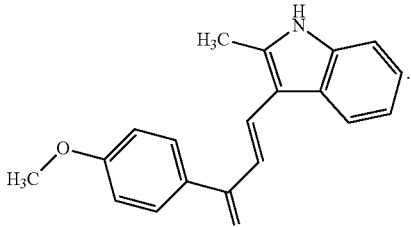

1-(4-methoxyphenyl)-3-(2-methyl-1H-indol-3-yl)-2-
propen-1-one

In an aspect of this embodiment, a compound of formula XIII disclosed herein has a structure of formula XIIIb

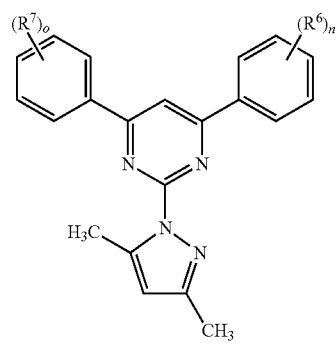

XIIIb wherein $R^6$ and $R^7$ are each independently H, OH, $C_{1-6}$ alkyl, $OC_{1-6}$ alkyl, $CO_2C_{1-6}$ alkyl, halogen, $NO_2$, or $SO_2$; n is 0 to 5; and o is 0 to 5.

In an aspect of this embodiment, a compound of formula XIII or formula XIIIb disclosed herein is

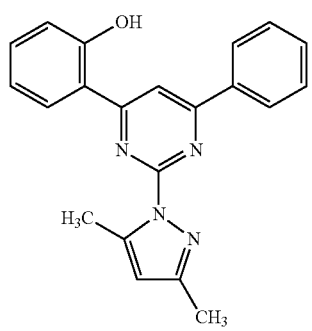

2-[2-(3,5-dimethyl-1H-pyrazol-1-yl)-6-phenyl-4-pyrimidinyl]phenol.

In some embodiments, a honeybee repellent may be optionally substituted 1-benzyl-4-(4-methoxy-2,3-dimethylbenzyl) piperazine. In some embodiments, a honeybee repellent may be optionally substituted 1-[(6-nitro-1,3-benzodioxol-5-yl)methyl]-4-phenylpiperazine. In some embodiments, a honeybee repellent may be optionally substituted 4-[4-nitro-3-(2-phenoxyethoxy)phenyl]morpholine. In some embodiments, a honeybee repellent may be optionally substituted 1-(3-chlorophenyl)-4-[(6-nitro-1,3-benzodioxol-5-yl)methyl]piperazine. In some embodiments, a honeybee repellent may be optionally substituted 1-(4-methoxybenzyl)-4-(3-methylbenzyl)piperazine. In some embodiments, a honeybee repellent may be optionally substituted 4-(4-methoxy-2,3-dimethylbenzyl) morpholine. In some embodiments, a honeybee repellent may be optionally substituted 1-benzyl-4-(4-methoxy-3-methylbenzyl)piperazine. In some embodiments, a honeybee repellent may be optionally substituted 1-(4-methoxy-2,3-dimethylbenzyl)-4-methyl piperazine. In some embodiments, a honeybee repellent may be optionally substituted 1-(4-methoxy-2,3-dimethylbenzyl)-4-methylpiperazine. In some embodiments, a honeybee repellent may be optionally substituted 1-(1,3-benzodioxol-5-ylmethyl)-4-(4,5-dimethoxy-2-nitrobenzyl)piperazine. In some embodiments, a honeybee repellent may be optionally substituted 1-(2,3-dimethylphenyl)-4-(4-methoxy-2,3-dimethylbenzyl)piperazine. In some embodiments, a honeybee repellent may be optionally substituted 1-(4-methoxy-2,3-dimethylbenzyl)-4-phenylpiperazine. In some embodiments, a honeybee repellent may be optionally substituted 1-[3-(4-iodophenoxy)propyl]piperidine. In some embodiments, a honeybee repellent may be optionally substituted 1-(4-methoxy-2,3-dimethylbenzyl)-4-(4-methylphenyl) piperazine.

In some embodiments, a honeybee repellent is not 1-benzyl-4-(4-methoxy-2,3-dimethylbenzyl) piperazine. In some embodiments, a honeybee repellent is not 1-[(6-nitro-1,3-benzodioxol-5-yl)methyl]-4-phenylpiperazine. In some embodiments, a honeybee repellent is not 4-[4-nitro-3-(2-phenoxyethoxy)phenyl]morpholine. In some embodiments, a honeybee repellent is not 1-(3-chlorophenyl)-4-[(6-nitro-1,3-benzodioxol-5-yl)methyl]piperazine. In some embodiments, a honeybee repellent is not 1-(4-methoxybenzyl)-4-(3-methylbenzyl)piperazine. In some embodiments, a honeybee repellent is not 4-(4-methoxy-2,3-dimethylbenzyl) morpholine. In some embodiments, a honeybee repellent is not 1-benzyl-4-(4-methoxy-3-methylbenzyl)piperazine. In some embodiments, a honeybee repellent is not 1-(4-methoxy-2,3-dimethylbenzyl)-4-methyl piperazine. In some embodiments, a honeybee repellent is not 1-(4-methoxy-2,3-dimethylbenzyl)-4-methylpiperazine. In some embodiments, a honeybee repellent is not 1-(1,3-benzodioxol-5-ylmethyl)-4-(4,5-dimethoxy-2-nitrobenzyl)piperazine. In some embodiments, a honeybee repellent is not 1-(2,3-dimethylphenyl)-4-(4-methoxy-2,3-dimethylbenzyl) piperazine. In some embodiments, a honeybee repellent is not 1-(4-methoxy-2,3-dimethylbenzyl)-4-phenylpiperazine. In some embodiments, a honeybee repellent is not 1-[3-(4-iodophenoxy)propyl]piperidine. In some embodiments, a honeybee repellent is not 1-(4-methoxy-2,3-dimethylbenzyl)-4-(4-methylphenyl)piperazine.

In some embodiments, a honeybee repellent may be optionally substituted 2-{[(2-methoxy-1-naphthyl)methylene]amino}-1H-isoindole-1,3(2H)-dione. In some embodiments, a honeybee repellent may be optionally substituted 2-[(2-ethoxybenzylidene)amino]-1H-isoindole-1,3(2H)-dione. In some embodiments, a honeybee repellent may be optionally substituted 3-ethyl-5-(4-hydroxybenzylidene)-2-thioxo-1,3-thiazolidin-4-one. In some embodiments, a honeybee repellent may be optionally substituted 3-butyl-5-(3-hydroxybenzylidene)-2-thioxo-1,3-thiazolidin-4-one. In some embodiments, a honeybee repellent may be optionally substituted 5-(3-bromo-4-methoxybenzylidene)-3-methyl-2-thioxo-1,3-thiazolidin-4-one. In some embodiments, a honeybee repellent may be optionally substituted 5-(5-bromo-2-hydroxybenzylidene)-3-ethyl-2-thioxo-1,3-thiazolidin-4-one. In some embodiments, a honeybee repellent may be optionally substituted 2-phenyl-4-(2-thienylmethylene)-1,3-oxazol-5(4H)-one. In some embodiments, a honeybee repellent may be optionally substituted 5-(4-chlorobenzylidene)-3-(2-methoxyphenyl)-2-thioxo-1,3-thiazolidin-4-one. In some embodiments, a honeybee repellent may be optionally substituted 3-(4-bromophenyl)-5-(4-hydroxybenzylidene)-2-thioxo-1,3-thiazolidin-4-one. In some embodiments, a honeybee repellent may be optionally substituted 4-[3-bromo-4-(dimethylamino)benzylidene]-2-(2-methoxyphenyl)-1,3-oxazol-5(4H)-one.

In some embodiments, a honeybee repellent is not 2-{[(2-methoxy-1-naphthyl)methylene]amino}-1H-isoindole-1,3(2H)-dione. In some embodiments, a honeybee repellent is not 2-[(2-ethoxybenzylidene)amino]-1H-isoindole-1,3(2H)-dione. In some embodiments, a honeybee repellent is not 3-ethyl-5-(4-hydroxybenzylidene)-2-thioxo-1,3-thiazolidin-4-one. In some embodiments, a honeybee repellent is not 3-butyl-5-(3-hydroxybenzylidene)-2-thioxo-1,3-thiazolidin-4-one. In some embodiments, a honeybee repellent is not 5-(3-bromo-4-methoxybenzylidene)-3-methyl-2-thioxo-1,3-thiazolidin-4-one. In some embodiments, a honeybee repellent is not 5-(5-bromo-2-hydroxybenzylidene)-3-ethyl-2-thioxo-1,3-thiazolidin-4-one. In some embodiments, a honeybee repellent is not 2-phenyl-4-(2-thienylmethylene)-1,3-oxazol-5(4H)-one. In some embodiments, a honeybee repellent is not 5-(4-chlorobenzylidene)-3-(2-methoxyphenyl)-2-thioxo-1,3-thiazolidin-4-one. In some embodiments, a honeybee repellent is not 3-(4-bromophenyl)-5-(4-hydroxybenzylidene)-2-thioxo-1,3-thiazolidin-4-one. In some embodiments, a honeybee repellent is not 4-[3-bromo-4-(dimethylamino)benzylidene]-2-(2-methoxyphenyl)-1,3-oxazol-5(4H)-one.

In some embodiments, a honeybee repellent may be optionally substituted 4-[2-(4-nitrophenyl)vinyl]phenol. In some embodiments, a honeybee repellent may be optionally substituted 3-{2-[(4-fluorobenzyl)amino]phenyl}-2(1H)-quinoxalinone. In some embodiments, a honeybee repellent may be optionally substituted 4-bromo-3-chlorophenyl)(4-ethoxybenzylidene)amine. In some embodiments, a honeybee repellent may be optionally substituted 4-[(2-chloro-5-nitrobenzylidene)amino]phenol. In some embodiments, a honeybee repellent may be optionally substituted 2-[(2-hydroxy-3,5-diiodobenzylidene)amino]-4,6-dimethylphenol. In some embodiments, a honeybee repellent may be optionally substituted (2-methoxybenzyl)(4-methoxy-3-biphenylyl)amine. In some embodiments, a honeybee repellent may be optionally substituted 2-{[(5-ethyl-2-hydroxyphenyl)imino]methyl}-4,6-diiodophenol.

In some embodiments, a honeybee repellent is not 4-[2-(4-nitrophenyl)vinyl]phenol. In some embodiments, a honeybee repellent is not 3-{2-[(4-fluorobenzyl)amino]phenyl}-2(1H)-quinoxalinone. In some embodiments, a honeybee repellent is not 4-bromo-3-chlorophenyl)(4-ethoxybenzylidene)amine. In some embodiments, a honeybee repellent is not 4-[(2-chloro-5-nitrobenzylidene)amino]phenol. In some embodiments, a honeybee repellent is not 2-[(2-hydroxy-3,5-diiodobenzylidene)amino]-4,6-dimethylphenol. In some embodiments, a honeybee repellent is not (2-methoxybenzyl)(4-methoxy-3-biphenylyl)amine. In some embodiments, a honeybee repellent is not 2-{[(5-ethyl-2-hydroxyphenyl)imino]methyl}-4,6-diiodophenol.

In some embodiments, a honeybee repellent may be optionally substituted 3-methoxy-4-(4-nitrophenoxy)benzaldehyde oxime. In some embodiments, a honeybee repellent is not 3-methoxy-4-(4-nitrophenoxy)benzaldehyde oxime.

In some embodiments, a honeybee repellent may be optionally substituted 1-butyl-4-hydroxy-2-oxo-N-(2-pyridinylmethyl)-1,2-dihydro-3-quinolinecarboxamide. In some embodiments, a honeybee repellent may be optionally substituted 2-acetyl-4-chlorophenyl 4-methylbenzoate. In some embodiments, a honeybee repellent may be optionally substituted N-(2-fluorobenzyl)-4-hydroxy-2-oxo-1-propyl-1,2-dihydro-3-quinolinecarboxamide. In some embodiments, a honeybee repellent may be optionally substituted ethyl 2-(benzoylamino)-5-ethyl-3-thiophenecarboxylate.

In some embodiments, a honeybee repellent is not 1-butyl-4-hydroxy-2-oxo-N-(2-pyridinylmethyl)-1,2-dihydro-3-quinolinecarboxamide. In some embodiments, a honeybee repellent is not 2-acetyl-4-chlorophenyl 4-methylbenzoate. In some embodiments, a honeybee repellent is not N-(2-fluorobenzyl)-4-hydroxy-2-oxo-1-propyl-1,2-dihydro-3-quinolinecarboxamide. In some embodiments, a honeybee repellent is not ethyl 2-(benzoylamino)-5-ethyl-3-thiophenecarboxylate.

In some embodiments, a honeybee repellent may be optionally substituted 2-(benzoylamino)-N-(2-chlorophenyl)benzamide. In some embodiments, a honeybee repellent is not 2-(benzoylamino)-N-(2-chlorophenyl)benzamide.

In some embodiments, a honeybee repellent may be optionally substituted ethyl 2-(3-aminophenyl)-4-quinolinecarboxylate. In some embodiments, a honeybee repellent is not ethyl 2-(3-aminophenyl)-4-quinolinecarboxylate.

In some embodiments, a honeybee repellent may be optionally substituted 1-(4-bromobenzoyl)-2,2,4-trimethyl-1,2-dihydroquinoline. In some embodiments, a honeybee repellent is not 1-(4-bromobenzoyl)-2,2,4-trimethyl-1,2-dihydroquinoline.

In some embodiments, a honeybee repellent may be optionally substituted dimethyl 2-(1,2,2-trimethyl-3-thioxo-2,3-dihydro-4(1H)-quinolinylidene)-1,3-dithiole-4,5-dicarboxylate. In some embodiments, a honeybee repellent may be optionally substituted dimethyl 2-(2,2,7-trimethyl-3-thioxo-2,3-dihydro-4(1H)-quinolinylidene)-1,3-dithiole-4,5-dicarboxylate.

In some embodiments, a honeybee repellent is not dimethyl 2-(1,2,2-trimethyl-3-thioxo-2,3-dihydro-4(1H)-quinolinylidene)-1,3-dithiole-4,5-dicarboxylate. In some embodiments, a honeybee repellent is not dimethyl 2-(2,2,7-trimethyl-3-thioxo-2,3-dihydro-4(1H)-quinolinylidene)-1,3-dithiole-4,5-dicarboxylate.

In some embodiments, a honeybee repellent may be optionally substituted N-(4-methoxy-2,3-dimethylbenzyl)-N,N',N'-trimethyl-1,2-ethanediamine. In some embodiments, a honeybee repellent is not N-(4-methoxy-2,3-dimethylbenzyl)-N, N',N'-trimethyl-1,2-ethanediamine.

In some embodiments, a honeybee repellent may be optionally substituted 1,2,3-trichloro-4-(isopropylamino)anthra-9,10-quinone. In some embodiments, a honeybee repellent is not 1,2,3-trichloro-4-(isopropylamino)anthra-9,10-quinone.

In some embodiments, a honeybee repellent may be optionally substituted [1-(3-nitrobenzyl)-3-piperidinyl]methyl 3-phenylacrylate. In some embodiments, a honeybee repellent is not [1-(3-nitrobenzyl)-3-piperidinyl]methyl 3-phenylacrylate.

In some embodiments, a honeybee repellent may be optionally substituted (3-amino-4,6-dimethylthieno[2,3-b]pyridin-2-yl) (4-chlorophenyl)methanone. In some embodiments, a honeybee repellent may be optionally substituted (4-bromophenyl)(5-methoxy-2-methyl-1-benzofuran-3-yl)methanone. In some embodiments, a honeybee repellent may be optionally substituted 1-(4-methoxyphenyl)-3-(2-methyl-1H-indol-3-yl)-2-propen-1-one. In some embodiments, a honeybee repellent may be optionally substituted 2-[2-(3,5-dimethyl-1H-pyrazol-1-yl)-6-phenyl-4-pyrimidinyl]phenol.

In some embodiments, a honeybee repellent is not (3-amino-4,6-dimethylthieno[2,3-b]pyridin-2-yl) (4-chlorophenyl)methanone. In some embodiments, a honeybee repellent is not (4-bromophenyl)(5-methoxy-2-methyl-1-benzofuran-3-yl)methanone. In some embodiments, a honeybee repellent is not 1-(4-methoxyphenyl)-3-(2-methyl-1H-indol-3-yl)-2-propen-1-one. In some embodiments, a honeybee repellent is not 2-[2-(3,5-dimethyl-1H-pyrazol-1-yl)-6-phenyl-4-pyrimidinyl]phenol.

Aspects of the present specification provide, in part, a composition comprising a honeybee repellent disclosed herein. A composition disclosed herein comprises a repellent compound disclosed herein and is useful in repelling honeybees from an individual and/or a location treated with the composition. As such, a composition disclosed herein is useful for any application that reduces bee-human interaction or a bee-location interaction. A composition may be administered to an individual or location alone, or in combination with other supplementary active ingredients, agents, or drugs.

A composition disclosed herein may comprise one or more honeybee repellents disclosed herein. In one embodiment, a composition disclosed herein may comprise only a single a honeybee repellent disclosed herein. In another embodiment, a composition disclosed herein may comprise a plurality of honeybee repellents disclosed herein. In aspects of this embodiment, a composition disclosed herein comprises at least two honeybee repellents, at least three honeybee repellents, at least four honeybee repellents, or at least five honeybee repellents. In other aspects of this embodiment, a composition disclosed herein comprises at most two honeybee repellents, at most three honeybee repellents, or at most four honeybee repellents. In yet other aspects of this embodiment, a composition disclosed herein comprises one to three honeybee repellents, two to four honeybee repellents, two to five honeybee repellents, three to five honeybee repellents, or two to three honeybee repellents.

In an embodiment, a composition disclosed herein includes a repellent of formula I, formula II, formula III, formula IV, formula V, formula VI, formula VII, formula VIII, formula IX, formula X, formula XI, formula XII, formula XIII, or any combination thereof.

In an embodiment, a composition disclosed herein has a honeybee repellency activity. In aspects of this embodiment, presence of a composition repels honeybees by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the composition present. In other aspects of this embodiment, presence of a composition repels honeybees by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, as compared to not having the composition present.

In an embodiment, a composition disclosed herein reduces a honeybee interaction with a mammal or location. In aspects of this embodiment, a composition reduces honeybee interaction with a mammal or location by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a composition reduces honeybee interaction with a mammal or location by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a composition disclosed herein reduces an ability of a honeybee to obtain a meal from a plant. In aspects of this embodiment, a composition reduces an ability of a honeybee to obtain a meal from a plant by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In other aspects of this embodiment, a composition reduces an ability of a honeybee to obtain a meal from a plant by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A composition disclosed herein can take any of a variety of dosage forms including, without limitation, a liquid composition, such as, e.g., a solution, suspension, emulsion; a semi-solid composition, such as, e.g., a ointment, cream, balm, foam, gel, or salve or a solid composition, such as, e.g., lyophilizate, powder, granule, pellet, capsule; or any other dosage form suitable for applying a repellent compound disclosed herein to a mammal, plant, and/or location to be treated. In one embodiment, in liquid, semi-solid, and solid forms, an amount of a repellent compound disclosed herein typically is between about 0.0001% (w/v) to about 50% (w/v), about 0.001% (w/v) to about 10.0% (w/v), or about 0.01% (w/v) to about 1.0% (w/v). In another aspect embodiment, in liquid, semi-solid, and solid forms, an amount of a repellent compound disclosed herein typically is between about 0.001 µg/cm$^2$ to about 500 µg/cm$^2$, about 0.01 µg/cm$^2$ to about 100 µg/cm$^2$, or about 0.1 µg/cm$^2$ to about 10 µg/cm$^2$. In another aspect embodiment, in liquid, semi-solid, and solid forms, an amount of a repellent compound disclosed herein typically is between about 0.01 nmole/cm$^2$ to about 1000 nmole/cm$^2$, about 0.1 nmole/cm$^2$ to about 100 nmole/cm$^2$, or about 1 nmole/cm$^2$ to about 50 nmole/cm$^2$. In another embodiment, in liquid, semi-solid, and solid forms, an amount of a repellent compound disclosed herein is typically is between about 0.001 mg/L to about 500 mg/L, about 0.01 mg/L to about 100 mg/L, or about 0.1 mg/L to about 50 mg/L.

The amount of a honeybee repellent disclosed herein used in the compositions disclosed herein is an effective amount. As used herein, the term "effective amount" refers to an amount of a honeybee repellent or composition disclosed herein sufficient to repel or direct movement of honeybees to the source of repellent compound release.

In aspects of this embodiment, a composition comprises a honeybee repellent in an effective amount of, e.g., at least 0.0001%, at least 0.00025%, at least 0.0005%, at least 0.00075%, at least 0.001%, at least 0.0025%, at least 0.005%, at least 0.0075%, at least 0.01%, at least 0.025%, at least 0.05%, at least 0.075%, at least 0.1%, at least 0.25%, at least 0.5%, at least 0.75%, at least 1%, at least 2.5%, at least 5%, at least 7.5%, at least 10%, at least 25%, or at least 50%, by weight of a composition.

In other aspects of this embodiment, a composition comprises a honeybee repellent in an effective amount of between, e.g., about 0.0001% to about 0.001%, about 0.0001% to about 0.01%, about 0.0001% to about 0.1%, about 0.00025% to about 0.0025%, about 0.00025% to about 0.025%, about 0.00025% to about 0.25%, about 0.0005% to about 0.005%, about 0.0005% to about 0.05%, about 0.0005% to about 0.75%, about 0.00075% to about 0.0075%, about 0.00075% to about 0.075%, about 0.00075% to about 0.75%, about 0.001% to about 0.01%, about 0.001% to about 0.1%, about 0.001% to about 1%, about 0.0025% to about 0.025%, about 0.0025% to about 0.25%, about 0.0025% to about 2.5%, about 0.005% to about 0.05%, about 0.005% to about 0.5%, about 0.005% to about 5%, about 0.0075% to about 0.075%, about 0.0075% to about 0.75%, about 0.0075% to about 7.5%, about 0.01% to about 0.1%, about 0.01% to about 1%, about 0.01% to about 10%, about 0.025% to about 0.25%, about 0.025% to about 2.5%, about 0.025% to about 25%, about 0.05% to about 0.5%, about 0.05% to about 5%, about 0.05% to about 50%, about 0.075% to about 0.75%, about 0.075% to about 7.5%, or about 0.075% to about 75%, by weight of a composition. In yet other aspects of this embodiment, a composition comprises a honeybee repellent in an effective amount of between, e.g., about 0.005% to about 0.015%, about 0.0025% to about 0.025%, or about 0.006% to about 0.016%, by weight of a composition.

A composition disclosed herein may optionally comprise one or more additional compounds providing an additional beneficial or otherwise useful effect. Such compounds include, without limitation, an adhesive, a solvent, a wetting agent, an emulsifying agent, a carrier, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof. Such compounds are known to a person of ordinary skill in the art.

In one aspect of this embodiment, a composition disclosed herein may optionally comprise an insecticide. In another aspect of this embodiment, a composition disclosed herein may optionally comprise a plurality of insecticides. Insecticides include oils, emulsifers, detergents, soaps, microorganisms like fungi, bacteria, bacteriophages, and viruses, abrasives, toxins, and poisons. Non-limiting examples of an insecticide include a organochlorine, such as, e.g., Aldrin, Chlordane, Chlordecone, DDT, Dieldrin, Endosulfan, Endrin, Heptachlor, Hexachlorobenzene, Lindane (gamma-hexachlorocyclohexane), Methoxychlor, Mirex, Pentachlorophenol, and TDE; an organophosphate, such as, e.g., Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Mevinphos, Monocrotophos, Naled, Omethoate, Oxydemeton-methyl, Parathion, Parathion-methyl, Phorate, Phosalone, Phosmet, Phostebupirim, Phoxim, Pirimiphos-methyl, Profenofos, Terbufos, Tetrachlorvinphos, Tribufos, and Trichlorfon; a carbamate, such as, e.g., Aldicarb, Bendiocarb, Carbofuran, Carbaryl, Dioxacarb, Fenobucarb, Fenoxycarb, Isoprocarb, Methomyl, and 2-(1-Methylpropyl)phenyl methylcarbamate; a pyrethroid, such as, e.g., Allethrin, Bifenthrin, Cyhalothrin, A-Cyhalothrin, Cypermethrin, Cyfluthrin, Deltamethrin, Etofenprox, Fenvalerate, Permethrin, Phenothrin, Prallethrin, Resmethrin, Tetramethrin, Tralomethrin, and Transfluthrin; a neonicotinoid, such as, e.g., Acetamiprid, Clothianidin, Imidacloprid, Nitenpyram, Nithiazine, Thiacloprid, and Thiamethoxam; and a spinosad, such as, e.g., spinosyn A and spinosyn B.

The present specification provides, in part, a composition comprising a repellent compound or a composition providing an additional beneficial or otherwise useful effect that is coated, encapsulated or otherwise covered with a honeybee repellent or a composition comprising a honeybee repellent disclosed herein. Additionally, the present specification provides, in part, a composition comprising a honeybee repellent or a composition comprising a honeybee repellent disclosed herein that is coated, encapsulated or otherwise covered with another compound or composition providing an additional beneficial or otherwise useful effect. The compositions disclosed herein are formulated to repel honeybees from a location where the compositions were intentionally or unintentionally deposited and at the same time provide an additional beneficial or otherwise useful effect.

When used to coat another substance, a honeybee repellent or composition comprising a honeybee repellent disclosed herein, or a compound or composition providing an additional beneficial or otherwise useful effect disclosed herein are formulated in a manner that will allow the repellent, compound, or compositions thereof to adhere to the other substance. Typically, a repellent, a compound, or a composition thereof are mixed with a coating material and processed into a formulation such as, e.g., a solid, a gel, a liquid, a suspension in aqueous or non-aqueous medium, an emulsion, or a foam. Such coating materials and adhering methods are known to a person of ordinary skill in the art.

For example, a honeybee repellent can be mixed with a wax and the resulting mixture is then adhered to a compound providing an additional beneficial or otherwise useful effect in a manner that ensures the compound is coated, encapsulated or otherwise covered by the mixture. In one aspect, a honeybee repellent can be mixed with a wax and the resulting mixture is then adhered to a seed in a manner that ensures the seed is coated, encapsulated or otherwise covered by the mixture. In another aspect, a honeybee repellent can be mixed with a wax and the resulting mixture is then adhered to an insecticide in a manner that ensures the insecticide is coated, encapsulated or otherwise covered by the mixture. In yet another aspect, a honeybee repellent and an insecticide can be mixed with a wax and the resulting mixture is then adhered to a seed in a manner that ensures the seed is coated, encapsulated or otherwise covered by the mixture.

In another embodiment, an appropriate amount of a honeybee repellent disclosed herein can be dissolved into an appropriate compatible solvent and the resulting mixture is then adhered to a compound providing an additional beneficial or otherwise useful effect in a manner that ensures the compound is coated, encapsulated or otherwise covered by the mixture. The solvent employed is typically a volatile solvent (i.e., having a boiling point of about 100° C. or less) that will evaporate over a period of time. In one aspect, a honeybee repellent can be mixed with a solvent and the resulting mixture is then adhered to a seed in a manner that ensures the seed is coated, encapsulated or otherwise covered by the mixture. In another aspect, a honeybee repellent can be mixed with a solvent and the resulting mixture is then adhered to an insecticide in a manner that ensures the insecticide is coated, encapsulated or otherwise covered by the mixture. In yet another aspect, a honeybee repellent and an insecticide can be mixed with a solvent and the resulting mixture is then adhered to a seed in a manner that ensures the seed is coated, encapsulated or otherwise covered by the mixture.

In one aspect of this embodiment, one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, larvicides, seeds, and any combination thereof is coated, encapsulated or otherwise covered with one or more honeybee repellents or compositions comprising a honeybee repellent disclosed herein.

In another aspect of this embodiment, a honeybee repellent or compositions disclosed herein is coated, encapsulated or otherwise covered with one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, larvicides, seeds, and any combination thereof.

In yet another aspect of this embodiment, seeds are coated, encapsulated or otherwise covered with one or more honeybee repellents or compositions comprising a honeybee repellent disclosed herein. These compositions are formulated to repel honeybees from the seed, and thus from a field, yard, pot, area, or body of water onto which the seeds were intentionally or unintentionally present.

In still another aspect of this embodiment, seeds are coated, encapsulated or otherwise covered with one or more honeybee repellents or compositions comprising a honeybee repellent disclosed herein and one or more insecticides, pesticides, fungicides, fertilizers of a micronutrient or macronutrient nature, herbicides, feeding inhibitors, insect molting, insect mating, insect maturation inhibitors, nematocides, nutritional or horticultural supplements, or larvicides. These compositions are formulated to repel honeybees from the seed, and thus from a field, yard, pot, area, or body of water onto which the seeds were be intentionally or unintentionally present as well as provide an additional beneficial or otherwise useful effect.

In another embodiment, a honeybee repellent or composition disclosed herein is incorporated into a device. As used herein, the term "device" refers to any device designed to house and/or shelter, a honeybee repellent or compositions disclosed herein. A device disclosed herein may be a container, holder or other solid support onto or into which a honeybee repellent or composition disclosed herein. A device disclosed herein may be made form any biological or synthetic material, including, without limitation, paper, filter paper, wood, cork, cotton, plastic, polymer, metal, or glass.

Aspects of the present specification disclose a use of a honeybee repellent disclosed herein to repel a honeybee from a location treated with the honeybee repellent. In one embodiment, the disclosed use is a use of a honeybee repellent disclosed herein to repel a honeybee from foraging and/or collecting nectar from a flower of a plant treated with the honeybee repellent. In another embodiment, the disclosed use is a use of a honeybee repellent disclosed herein to repel a honeybee from a structure treated with the honeybee repellent.

Aspects of the present specification disclose a method of treating a location by applying a honeybee repellent disclosed herein, wherein such application repels a honeybee from the treated location. In one embodiment, the disclosed method is a method of treating a plant by applying a honeybee repellent disclosed herein, wherein such application repels a honeybee from foraging and/or collecting nectar from a flower of the treated plant. In another embodiment, the disclosed method is a method of treating a structure by applying a honeybee repellent disclosed herein, wherein such application repels a honeybee from the treated structure.

Aspects of the present specification disclose a method of reducing or preventing a honeybee foraging to a location by applying a honeybee repellent or composition disclosed herein, wherein such application repels honeybees from the location, thereby reducing or preventing the honeybee foraging. In one embodiment, the disclosed method is a method of treating a plant by applying a honeybee repellent or composition disclosed herein, wherein such application repels a honeybee from foraging for a meal in the vicinity of the treated plant, flower, or seed. In another embodiment, the disclosed method is a method of treating a structure by applying a honeybee repellent or composition disclosed herein, wherein such application repels a honeybee from foraging for a meal in the vicinity of the treated structure.

As used herein, the term "location" refers to any site to which movement of a honeybee is to be retarded. A location includes, by way of example, a plant or group of plants or part of a plant, a particular area of land, or a man-made structure, such as, e.g., a commercial building, a house, a shed, or other physical structure. As used herein, the term "plant" refers to any living organism belonging to the Kingdom Plantae. Non-limiting examples include trees, flowering plant, herbs, bushes, grasses, vines, ferns, mosses, and green algae. As used herein, the term "flower" is synonymous with "bloom" or "blossom" and refers the reproductive structure found in angiosperms. As used herein, the term "crop plant" refers to a plant that produces a crop. Non-limiting examples include are plants that produce fruits, seeds, nuts, grains, oil, wood, and fibers. As used herein, the term "crop" refers to a plant product which is of economical value. Non-limiting examples include are fruits, seeds, nuts, grains, oil, wood, and fibers.

A honeybee repellent or composition disclosed herein is applied to a location by any method that can dispense to a location an amount of honeybee repellent effective in repelling a honeybee. A method of application is not critical and many well known methods can be used. In one embodiment, an appropriate amount of a honeybee repellent or composition disclosed herein can be dissolved into an appropriate compatible solvent and dispensed as a solution onto the intended location. The solvent employed is typically a volatile solvent (i.e., having a boiling point of about 100° C. or less) that will evaporate over a period of time. In another embodiment, an appropriate amount of a honeybee repellent or composition disclosed herein can be combined with an appropriate propellant and used as a spray for application onto the intended location.

In another embodiment, a honeybee repellent or composition disclosed herein can be impregnated into a compatible matrix. As used herein, the term "compatible matrix" refers to any material in which one or more repellent compounds disclosed herein are either soluble or miscible and where the material does not significantly alter or degrade the attractant activity of the one or more repellent compound. In aspects of this embodiment, a compatible matrix does not significantly alter or degrade an attractant activity of one or more honeybee repellents over a period of, e.g., at least 7 days, at least 14 days, at least 21 days, at least 28 days, at least 35 days, at least 42 days, at least 49 days, at least 56 days, or at least 63 days. Impregnation of a repellent compound into the compatible matrix can be achieved by any well known methods known in the art. For example, a honeybee repellent can be dissolved into a compatible volatile solvent and the resulting solution added to the matrix whereupon evaporation of the solvent results in impregnation of the repellent compound into the compatible matrix. In this regard, the matrix can be cotton twine, polymers such as, e.g., polyvinyls, polyisoprenes, polyethylene, polypropylene or copolymers thereof, or polybutenes. In another example, a compatible matrix is thinned by heating and then a repellent compound is added directly thereto. The mixture can then be combined with twine or other compatible matrices. A compatible matrix disclosed herein may be employed by itself or incorporated into a device used to house the matrix.

In another embodiment, a honeybee repellent or composition disclosed herein can be incorporated into a controlled-release device which dispenses a honeybee repellent and/or other beneficial compound over time in a regulated or predictable manner. A controlled-release device disclosed herein may be employed by itself or incorporated into another device used to house the controlled-release device.

One type of controlled-release device is a "reservoir" device where a honeybee repellent or composition forms a core surrounded by an inert diffusion barrier. An inert diffusion barrier includes membranes which are non-porous, homogeneous polymeric films, through which transport occurs by a process of dissolution of the permeating species in the polymer at one interface and diffusion down a gradient in thermodynamic activity. These membranes are usually referred to as solution-diffusion membranes. Another class inert diffusion barrier includes the porous and/or fibrous barriers such as, for example, hollow fibers, porous and/or fibrous materials, in which a repellent compound diffuses mainly by capillary forces. Other less common reservoir devices are designed to enable diffusion to take place by mechanical pumping or under external forces, such as, e.g., gravity, electrical field, vacuum, or centrifugal forces. A reservoir device can exist in a variety of shapes, and can be degradable or non-degradable.

In an aspect of this embodiment, a reservoir device is a microcapsule comprising a core of a honeybee repellent or composition disclosed herein surrounded by a coating or shell of, e.g., a polyvinyl chloride (PVC)-polyvinyl acetate (PVA) plastic. Size typically varies from about 1 µm to about 1000 µm and can have irregular or geometric shapes. Core payload usually varies from 0.1 to 98 weight percent. Encapsulation processes are often loosely classified as either chemical or mechanical. Examples of chemical processes include but are not limited to complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes include but are not limited to spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Another type of controlled-release device is a "monolithic" device where a honeybee repellent or composition is dissolved or dispersed throughout a substantially inert matrix from which the repellent compound and/or other beneficial compound is gradually released. Non-limiting examples of matrices included in a monolithic device include various gels, waxes, gelatins, natural resins, rubbers, elastomers, synthetic and natural polymers. A monolithic device can exist in a variety of shapes, and can be degradable or non-degradable. Size can vary depending on the application. For example, a monolithic device can be produced as a microcapsule having a size of about 1 µm to about 1000 µm with irregular or geometric shapes. As another example, a monolithic device can have a size of about 1 mm to about 10 cm with irregular or geometric shape.

A controlled-release device disclosed herein can be a liquid composition or a solid composition. A liquid sustained-release formulation includes a honeybee repellent or composition disclosed herein, a solvent, and typically further comprise surface active agents to render the composition readily dispersible in water, such agents include a wetting agent, an emulsifying agent, or a dispersing agent. In one embodiment, a liquid form of a sustained-release formulation is an emulsion formulation, such as, e.g., a water in oil (w/o) emulsion or oil in water (o/w) emulsion. Non-limiting examples of oils include vegetable oils and mineral oils. Droplet size can vary from the nanometer scale (colloidal dispersion) to several hundred microns. A variety of surfactants and thickeners are usually incorporated in the formulation to modify the size of the droplets, stabilize the emulsion, and modify the release.

A solid form of controlled-release device comprises a solid substrate like porous particulates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a repellent compound disclosed herein through the walls, capillary tubing which releases the compound out of an opening in the tubing, polymeric blocks of different shapes, e.g., strips, blocks, tablets, discs, which release the compound out of the polymer matrix, membrane systems which hold the repellent compound within an impermeable container and release it through a measured permeable membrane, and combinations of the foregoing. Examples of other dispensing means are polymer laminates, polyvinyl chloride pellets, and microcapillaries.

Controlled release can also be achieved by a number of other methods such as, e.g., complexation of a honeybee repellent or composition, slowly dissolving coatings, erosion, microbial action, or use of derivatives or new compounds of reduced solubility or volatility.

In aspects of this embodiment, a controlled-release device releases a honeybee repellent or composition disclosed herein with substantially zero order release kinetics over a period of, e.g., about 7 days, about 15 days, about 30 days, about 45 days, about 60 days, about 75 days, or about 90 days. In other aspects of this embodiment, a controlled-release device releases a honeybee repellent or composition disclosed herein with substantially zero order release kinetics over a period of, e.g., at least 7 days, at least 15 days, at least 30 days, at least 45 days, at least 60 days, at least 75 days, or at least 90 days. In other aspects of this embodiment, a controlled-release device releases a honeybee repellent or composition disclosed herein with substantially zero order release kinetics over a period of between, e.g., about 7 days to about 30 days, about 15 days to about 45 days, about 30 days to about 60 days, about 45 days to about 75 days, or about 60 days to about 90 days.

In aspects of this embodiment, a controlled-release device releases a honeybee repellent or composition disclosed herein with substantially first order release kinetics over a period of, e.g., about 7 days, about 15 days, about 30 days, about 45 days, about 60 days, about 75 days, or about 90 days. In other aspects of this embodiment, a controlled-release device releases a honeybee repellent or composition disclosed herein with substantially first order release kinetics over a period of, e.g., at least 7 days, at least 15 days, at least 30 days, at least 45 days, at least 60 days, at least 75 days, or at least 90 days. In other aspects of this embodiment, a controlled-release device releases a honeybee repellent or composition disclosed herein with substantially first order release kinetics over a period of between, e.g., about 7 days to about 30 days, about 15 days to about 45 days, about 30 days to about 60 days, about 45 days to about 75 days, or about 60 days to about 90 days.

Regardless of the method of application, the amount of a honeybee repellent disclosed herein used is a repellent effective amount, i.e., it is an amount sufficient to retard the movement of honeybees to the selected location. In aspects of this embodiment, a honeybee repellent disclosed herein is applied at a rate of, e.g., about 0.01 $mg/m^2$, about 0.025 $mg/m^2$, about 0.05 $mg/m^2$, about 0.075 $mg/m^2$, about 0.1 $mg/m^2$, about 0.25 $mg/m^2$, about 0.5 $mg/m^2$, about 0.75 $mg/m^2$, about 1 $mg/m^2$, about 2.5 $mg/m^2$, about 5 $mg/m^2$, about 7.5 $mg/m^2$, or about 10 $mg/m^2$. In other aspects of this embodiment, a honeybee repellent disclosed herein is applied at a rate of, e.g., at least 0.01 $mg/m^2$, at least 0.025 $mg/m^2$, at least 0.05 $mg/m^2$, at least 0.075 $mg/m^2$, at least 0.1 $mg/m^2$, at least 0.25 $mg/m^2$, at least 0.5 $mg/m^2$, at least 0.75 $mg/m^2$, at least 1 $mg/m^2$, at least 2.5 $mg/m^2$, at least 5 $mg/m^2$, at least 7.5 $mg/m^2$, or at least 10 $mg/m^2$. In yet other aspects of this embodiment, a honeybee repellent disclosed herein is applied at a rate of, between e.g., about 0.01 $mg/m^2$ to about 10 $mg/m^2$, about 0.01 $mg/m^2$ to about 1 $mg/m^2$, about 0.01 $mg/m^2$ to about 0.1 $mg/m^2$, about 0.05 $mg/m^2$ to about 10 $mg/m^2$, about 0.05 $mg/m^2$ to about 1 $mg/m^2$, about 0.05 $mg/m^2$ to about 0.1 $mg/m^2$, about 0.05 $mg/m^2$ to about 5 $mg/m^2$, or about 0.05 $mg/m^2$ to about 0.5 $mg/m^2$.

Aspects of the present specification may also be described as follows:

1. A honeybee repellent that substantially mimics a repellent chemosensory cue of 2-heptanone, wherein the compound is not 2-heptanone.
2. The honeybee repellent according to embodiment 1, wherein the honeybee repellent has a repellent chemosensory cue that is at least 75%, at least 80%, at least 85%, at least 90%, at least 95%, or at least 97% that of the repellent chemosensory cue of 2-heptanone.

3. The honeybee repellent according to embodiment 1, wherein the honeybee repellent has a repellent chemosensory cue that is at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold that of the repellent chemosensory cue of 2-heptanone.

4. A honeybee repellent having a honeybee repellency activity, wherein the compound is not 2-heptanone.

5. The honeybee repellent according to embodiment 4, wherein the honeybee repellent repels honeybees by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the honeybee repellent present.

6. The honeybee repellent according to embodiment 4 or 5, wherein the honeybee repellent reduces a honeybee interaction with a mammal, a plant, structure, and/or location.

7. The honeybee repellent according to any one of embodiments 4-6, wherein the honeybee repellent reduces a honeybee interaction with a mammal, a plant, structure, and/or location by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

8. The honeybee repellent according to any one of embodiments 4-7, wherein the honeybee repellent reduces an ability of a honeybee to obtain a meal and/or nectar from a plant.

9. The honeybee repellent according to any one of embodiments 4-8, wherein the honeybee repellent reduces an ability of a honeybee to obtain a meal and/or nectar from a plant by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

10. The honeybee repellent according to any one of embodiments 1-9, wherein the honeybee repellent is more stable than 2-heptanone.

11. The honeybee repellent according to any one of embodiments 1-10, wherein the honeybee repellent is less volatile than 2-heptanone.

12. The honeybee repellent according to any one of embodiments 1-11, wherein the honeybee repellent has a half-life of at least one day, at least three days, at least five days, at least one week, at least two weeks, at least three weeks, at least one month, at least two months, or at least three months.

13. The honeybee repellent according to embodiments 1-11, wherein the honeybee repellent has a half-life about one day to about seven days, about three days to about seven days, about five days to about seven days, about one week to about four weeks, about two weeks to about four weeks, about three weeks to about four weeks, about one month to about four months, about two months to about four months, or about three months to about four months.

14. The honeybee repellent according to any one of embodiments 1-13, wherein the honeybee repellent has a binding affinity for a honeybee OBP that is substantially the same as the binding affinity of 2-heptanone, wherein the compound is not 2-heptanone.

15. The honeybee repellent according to any one of embodiments 1-14, wherein the honeybee repellent has a binding affinity for a honeybee OBP that is at least 75%, at least 80%, at least 85%, at least 90%, at least 95%, or at least 97% that of the binding affinity of 2-heptanone for that honeybee OBP.

16. The honeybee repellent according to any one of embodiments 1-15, wherein the honeybee repellent has a dissociation equilibrium constant that is greater than the dissociation equilibrium constant of 2-heptanone for that honeybee OBP by at least one-fold, at least two-fold, at least three-fold, at least four fold, at least five-fold, at least six-fold, at least seven-fold, at least eight-fold, at least nine-fold, at least 10-fold, at least 20-fold, at least 30-fold, at least 40-fold, at least 50-fold, at least 60-fold, at least 70-fold, at least 80-fold, at least 90-fold, at least 100-fold, at least 125-fold, at least 150-fold, at least 175-fold, or at least 200-fold.

17. The honeybee repellent according to any one of embodiments 1-16, wherein the honeybee repellent has an association rate constant of less than $1\times10^5$ $M^{-1}$ $s^{-1}$, less than $1\times10^6$ $M^{-1}$ $s^{-1}$, less than $1\times10^7 M^{-1}$ $s^{-1}$, or less than $1\times10^8$ $M^{-1}$ $s^{-1}$.

18. The honeybee repellent according to any one of embodiments 1-16, wherein the honeybee repellent has an association rate constant of more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$.

19. The honeybee repellent according to any one of embodiments 1-18, wherein the honeybee repellent has a disassociation rate constant of less than $1\times10^{-3}$ $s^{-1}$, less than $1\times10^{-4}$ $s^{-1}$, or less than $1\times10^{-5}$ $s^{-1}$.

20. The honeybee repellent according to any one of embodiments 1-18, wherein the honeybee repellent has a disassociation rate constant of more than $1\times10^{-3}$ $s^{-1}$, more than $1\times10^{-4}$ $s^{-1}$, or more than $1\times10^{-5}$ $s^{-1}$.

21. The honeybee repellent according to any one of embodiments 1-20, wherein the honeybee repellent has an equilibrium disassociation constant of less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM.

22. The honeybee repellent according to any one of embodiments 1-20, wherein the honeybee repellent has an equilibrium disassociation constant of more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

23. The honeybee repellent according to any one of embodiments 1-22, wherein the honeybee repellent has a structure of formula I disclosed herein 24. The honeybee repellent according to any one of embodiments 1-23, wherein the honeybee repellent wherein the compound has a structure of formula Ia disclosed herein.

25. The honeybee repellent according to any one of embodiments 1-24, wherein the honeybee repellent is 1-benzyl-4-(4-methoxy-2,3-dimethylbenzyl) piperazine, 1-[(6-nitro-1,3-benzodioxol-5-yl)methyl]-4-phenylpiperazine, 4-[4-nitro-3-(2-phenoxyethoxy)phenyl]morpholine, 1-(3-chlorophenyl)-4-[(6-nitro-1,3-benzodioxol-5-yl)methyl]

piperazine, 1-(4-methoxybenzyl)-4-(3-methylbenzyl)piperazine, 4-(4-methoxy-2,3-dimethylbenzyl) morpholine, 1-benzyl-4-(4-methoxy-3-methylbenzyl)piperazine, 1-(4-methoxy-2,3-dimethylbenzyl)-4-methyl piperazine, 1-(4-methoxy-2,3-dimethylbenzyl)-4-methylpiperazine, 1-(1,3-benzodioxol-5-ylmethyl)-4-(4,5-dimethoxy-2-nitrobenzyl)piperazine, 1-(2,3-dimethylphenyl)-4-(4-methoxy-2,3-dimethylbenzyl)piperazine, 1-(4-methoxy-2,3-dimethylbenzyl)-4-phenylpiperazine, 1-[3-(4-iodophenoxy)propyl]piperidine, 1-(4-methoxy-2,3-dimethylbenzyl)-4-(4-methylphenyl)piperazine, or any combination thereof.

26. The honeybee repellent according to any one of embodiments 1-22, wherein the honeybee repellent has a structure of formula II disclosed herein.

27. The honeybee repellent according to any one of embodiments 1-22 or 26, wherein the honeybee repellent has a structure of formula IIa disclosed herein.

28. The honeybee repellent according to any one of embodiments 1-22, 26 or 27, wherein the honeybee repellent has is 2-{[(2-methoxy-1-naphthyl)methylene]amino}-1H-isoindole-1,3(2H)-dione, 2-[(2-ethoxybenzylidene)amino]-1H-isoindole-1,3(2H)-dione, or any combination thereof.

29. The honeybee repellent according to any one of embodiments 1-22 or 26, wherein the honeybee repellent has a structure of formula IIb disclosed herein.

30. The honeybee repellent according to any one of embodiments 1-22, 26 or 29, wherein the honeybee repellent is 3-ethyl-5-(4-hydroxybenzylidene)-2-thioxo-1,3-thiazolidin-4-one, 3-butyl-5-(3-hydroxybenzylidene)-2-thioxo-1,3-thiazolidin-4-one, 5-(3-bromo-4-methoxybenzylidene)-3-methyl-2-thioxo-1,3-thiazolidin-4-one, 5-(5-bromo-2-hydroxybenzylidene)-3-ethyl-2-thioxo-1,3-thiazolidin-4-one, or any combination thereof.

31. The honeybee repellent according to any one of embodiments 1-22 or 26, wherein the honeybee repellent has a structure of formula IIc disclosed herein.

32. The honeybee repellent according to any one of embodiments 1-22, 26 or 31, wherein the honeybee repellent is 2-phenyl-4-(2-thienylmethylene)-1,3-oxazol-5(4H)-one.

33. The honeybee repellent according to any one of embodiments 1-22 or 26, wherein the honeybee repellent has a structure of formula IId disclosed herein.

34. The honeybee repellent according to any one of embodiments 1-22, 26 or 33, wherein the honeybee repellent is 5-(4-chlorobenzylidene)-3-(2-methoxyphenyl)-2-thioxo-1,3-thiazolidin-4-one, 3-(4-bromophenyl)-5-(4-hydroxybenzylidene)-2-thioxo-1,3-thiazolidin-4-one, 4-[3-bromo-4-(dimethylamino)benzylidene]-2-(2-methoxyphenyl)-1,3-oxazol-5(4H)-one, or any combination thereof.

35. The honeybee repellent according to any one of embodiments 1-22, wherein the honeybee repellent has a structure of formula III disclosed herein.

36. The honeybee repellent according to any one of embodiments 1-22 or 35, wherein the honeybee repellent is 4-[2-(4-nitrophenyl)vinyl]phenol, 3-{2-[(4-fluorobenzyl)amino]phenyl}-2(1H)-quinoxalinone, 4-bromo-3-chlorophenyl)(4-ethoxybenzylidene)amine, 4-[(2-chloro-5-nitrobenzylidene)amino]phenol, 2-[(2-hydroxy-3,5-diiodobenzylidene)amino]-4,6-dimethylphenol, (2-methoxybenzyl)(4-methoxy-3-biphenylyl)amine, 2-{[(5-ethyl-2-hydroxyphenyl)imino]methyl}-4,6-diiodophenol, or any combination thereof.

37. The honeybee repellent according to any one of embodiments 1-22, wherein the honeybee repellent has a structure of formula IV disclosed herein.

38. The honeybee repellent according to any one of embodiments 1-22 or 37, wherein the honeybee repellent is 3-methoxy-4-(4-nitrophenoxy)benzaldehyde oxime.

39. The honeybee repellent according to any one of embodiments 1-22, wherein the honeybee repellent has a structure of formula V disclosed herein.

40. The honeybee repellent according to any one of embodiments 1-22 or 39, wherein the honeybee repellent has a structure of formula Va disclosed herein.

41. The honeybee repellent according to any one of embodiments 1-22 39 or 40, wherein the honeybee repellent is 1-butyl-4-hydroxy-2-oxo-N-(2-pyridinylmethyl)-1,2-dihydro-3-quinolinecarboxamide, 2-acetyl-4-chlorophenyl 4-methylbenzoate, N-(2-fluorobenzyl)-4-hydroxy-2-oxo-1-propyl-1,2-dihydro-3-quinolinecarboxamide, ethyl 2-(benzoylamino)-5-ethyl-3-thiophenecarboxylate, or any combination thereof.

41. The honeybee repellent according to any one of embodiments 1-22, wherein the honeybee repellent has a structure of formula VI disclosed herein.

42. The honeybee repellent according to any one of embodiments 1-22 or 41, wherein the honeybee repellent is 2-(benzoylamino)-N-(2-chlorophenyl)benzamide.

43. The honeybee repellent according to any one of embodiments 1-22, wherein the honeybee repellent has a structure of formula VII disclosed herein.

44. The honeybee repellent according to any one of embodiments 1-22 or 43, wherein the honeybee repellent is ethyl 2-(3-aminophenyl)-4-quinolinecarboxylate.

45. The honeybee repellent according to any one of embodiments 1-22, wherein the honeybee repellent has a structure of formula VIII disclosed herein.

46. The honeybee repellent according to any one of embodiments 1-22 or 45, wherein the honeybee repellent is 1-(4-bromobenzoyl)-2,2,4-trimethyl-1,2-dihydroquinoline.

47. The honeybee repellent according to any one of embodiments 1-22, wherein the honeybee repellent has a structure of formula IX disclosed herein.

48. The honeybee repellent according to any one of embodiments 1-22 or 47, wherein the honeybee repellent is dimethyl 2-(1,2,2-trimethyl-3-thioxo-2,3-dihydro-4(1H)-quinolinylidene)-1,3-dithiole-4,5-dicarboxylate, dimethyl 2-(2,2,7-trimethyl-3-thioxo-2,3-dihydro-4(1H)-quinolinylidene)-1,3-dithiole-4,5-dicarboxylate, or any combination thereof.

49. The honeybee repellent according to any one of embodiments 1-22, wherein the honeybee repellent has a structure of formula X disclosed herein.

50. The honeybee repellent according to any one of embodiments 1-22 or 49, wherein the honeybee repellent is N-(4-methoxy-2,3-dimethylbenzyl)-N,N',N'-trimethyl-1,2-ethanediamine.

51. The honeybee repellent according to any one of embodiments 1-22, wherein the honeybee repellent has a structure of formula XI disclosed herein.

52. The honeybee repellent according to any one of embodiments 1-22 or 51, wherein the honeybee repellent is 1,2,3-trichloro-4-(isopropylamino)anthra-9,10-quinone.

53. The honeybee repellent according to any one of embodiments 1-22, wherein the honeybee repellent has a structure of formula XII disclosed herein.

54. The honeybee repellent according to any one of embodiments 1-22 or 53, wherein the honeybee repellent is [1-(3-nitrobenzyl)-3-piperidinyl]methyl 3-phenylacrylate.

55. The honeybee repellent according to any one of embodiments 1-22, wherein the honeybee repellent has a structure of formula XIII disclosed herein.

56. The honeybee repellent according to any one of embodiments 1-22 or 55, wherein the honeybee repellent has a structure of formula XIIIa disclosed herein.

57. The compound according to any one of embodiments 1-22, 55 or 56, wherein the compound is (3-amino-4,6-dimethylthieno[2,3-b]pyridin-2-yl) (4-chlorophenyl)methanone, (4-bromophenyl)(5-methoxy-2-methyl-1-benzofuran-3-yl)methanone, 1-(4-methoxyphenyl)-3-(2-methyl-1H-indol-3-yl)-2-propen-1-one, 2-[2-(3,5-dimethyl-1H-pyrazol-1-yl)-6-phenyl-4-pyrimidinyl]phenol, or any combination thereof.

58. The honeybee repellent according to any one of embodiments 1-22 or 55, wherein the honeybee repellent has a structure of formula XIIIb disclosed herein.

59. The compound according to any one of embodiments 1-22, 55 or 58, wherein the honeybee repellent is 2-[2-(3,5-dimethyl-1H-pyrazol-1-yl)-6-phenyl-4-pyrimidinyl]phenol.

60. The honeybee repellent according to any one of embodiments 1-22, wherein the honeybee repellent has a structure of formula XV disclosed herein.

61. The honeybee repellent according to any one of embodiments 1-22 or 60, wherein the honeybee repellent has a structure of formula XVa disclosed herein.

62. The honeybee repellent according to any one of embodiments 1-22 or 60, wherein the honeybee repellent has a structure of formula XVb disclosed herein.

63. The honeybee repellent according to any one of embodiments 1-22 or 60, wherein the honeybee repellent has a structure of formula XVc disclosed herein.

64. The honeybee repellent according to any one of embodiments 1-22 or 60, wherein the honeybee repellent has a structure of formula XVd disclosed herein.

65. The honeybee repellent according to any one of embodiments 1-22, wherein the honeybee repellent is an optionally substituted 1-benzyl-4-(4-methoxy-2,3-dimethylbenzyl) piperazine, optionally substituted 1-[(6-nitro-1,3-benzodioxol-5-yl)methyl]-4-phenylpiperazine, an optionally substituted 4-[4-nitro-3-(2-phenoxyethoxy)phenyl]morpholine, an optionally substituted 1-(3-chlorophenyl)-4-[(6-nitro-1,3-benzodioxol-5-yl)methyl]piperazine, an optionally substituted 1-(4-methoxybenzyl)-4-(3-methylbenzyl)piperazine, an optionally substituted 4-(4-methoxy-2,3-dimethylbenzyl) morpholine, an optionally substituted 1-benzyl-4-(4-methoxy-3-methylbenzyl)piperazine, an optionally substituted 1-(4-methoxy-2,3-dimethylbenzyl)-4-methyl piperazine, an optionally substituted 1-(4-methoxy-2,3-dimethylbenzyl)-4-methylpiperazine, an optionally substituted 1-(1,3-benzodioxol-5-ylmethyl)-4-(4,5-dimethoxy-2-nitrobenzyl)piperazine, an optionally substituted 1-(2,3-dimethylphenyl)-4-(4-methoxy-2,3-dimethylbenzyl) piperazine, an optionally substituted 1-(4-methoxy-2,3-dimethylbenzyl)-4-phenylpiperazine, an optionally substituted 1-[3-(4-iodophenoxy)propyl]piperidine, an optionally substituted 1-(4-methoxy-2,3-dimethylbenzyl)-4-(4-methylphenyl)piperazine, an optionally substituted 2-{[(2-methoxy-1-naphthyl)methylene]amino}-1H-isoindole-1,3(2H)-dione, an optionally substituted 2-[(2-ethoxybenzylidene)amino]-1H-isoindole-1,3(2H)-dione, an optionally substituted 3-ethyl-5-(4-hydroxybenzylidene)-2-thioxo-1,3-thiazolidin-4-one, an optionally substituted 3-butyl-5-(3-hydroxybenzylidene)-2-thioxo-1,3-thiazolidin-4-one, an optionally substituted 5-(3-bromo-4-methoxybenzylidene)-3-methyl-2-thioxo-1,3-thiazolidin-4-one, an optionally substituted 5-(5-bromo-2-hydroxybenzylidene)-3-ethyl-2-thioxo-1,3-thiazolidin-4-one, an optionally substituted 2-phenyl-4-(2-thienylmethylene)-1,3-oxazol-5(4H)-one, an optionally substituted 5-(4-chlorobenzylidene)-3-(2-methoxyphenyl)-2-thioxo-1,3-thiazolidin-4-one, an optionally substituted 3-(4-bromophenyl)-5-(4-hydroxybenzylidene)-2-thioxo-1,3-thiazolidin-4-one, an optionally substituted 4-[3-bromo-4-(dimethylamino)benzylidene]-2-(2-methoxyphenyl)-1,3-oxazol-5(4H)-one, an optionally substituted 4-[2-(4-nitrophenyl)vinyl]phenol, an optionally substituted 3-{2-[(4-fluorobenzyl)amino]phenyl}-2(1H)-quinoxalinone, an optionally substituted 4-bromo-3-chlorophenyl)(4-ethoxybenzylidene)amine, an optionally substituted 4-[(2-chloro-5-nitrobenzylidene)amino]phenol, an optionally substituted 2-[(2-hydroxy-3,5-diiodobenzylidene)amino]-4,6-dimethylphenol, an optionally substituted (2-methoxybenzyl)(4-methoxy-3-biphenylyl)amine, an optionally substituted 2-{[(5-ethyl-2-hydroxyphenyl)imino]methyl}-4,6-diiodophenol, an optionally substituted 3-methoxy-4-(4-nitrophenoxy)benzaldehyde oxime. In some embodiments, a honeybee repellent may be optionally substituted 1-butyl-4-hydroxy-2-oxo-N-(2-pyridinylmethyl)-1,2-dihydro-3-quinolinecarboxamide, an optionally substituted 2-acetyl-4-chlorophenyl 4-methylbenzoate, an optionally substituted N-(2-fluorobenzyl)-4-hydroxy-2-oxo-1-propyl-1,2-dihydro-3-quinolinecarboxamide, an optionally substituted ethyl 2-(benzoylamino)-5-ethyl-3-thiophenecarboxylate, an optionally substituted 2-(benzoylamino)-N-(2-chlorophenyl)benzamide, an optionally substituted ethyl 2-(3-aminophenyl)-4-quinolinecarboxylate, an optionally substituted 1-(4-bromobenzoyl)-2,2,4-trimethyl-1,2-dihydroquinoline, an optionally substituted dimethyl 2-(1,2,2-trimethyl-3-thioxo-2,3-dihydro-4(1H)-quinolinylidene)-1,3-dithiole-4,5-dicarboxylate, an optionally substituted dimethyl 2-(2,2,7-trimethyl-3-thioxo-2,3-dihydro-4(1H)-quinolinylidene)-1,3-dithiole-4,5-dicarboxylate, an optionally substituted N-(4-methoxy-2,3-dimethylbenzyl)-N,N',N'-trimethyl-1,2-ethanediamine, an optionally substituted 1,2,3-trichloro-4-(isopropylamino)anthra-9,10-quinone, an optionally substituted [1-(3-nitrobenzyl)-3-piperidinyl]methyl 3-phenylacrylate, an optionally substituted (3-amino-4,6-dimethylthieno[2,3-b]pyridin-2-yl) (4-chlorophenyl)methanone, an optionally substituted (4-bromophenyl)(5-methoxy-2-methyl-1-benzofuran-3-yl)methanone, an optionally substituted 1-(4-methoxyphenyl)-3-(2-methyl-1H-indol-3-yl)-2-propen-1-one, or an optionally substituted 2-[2-(3,5-dimethyl-1H-pyrazol-1-yl)-6-phenyl-4-pyrimidinyl]phenol.

66. The honeybee repellent according to any one of embodiments 1-65, wherein the honeybee repellent is not 1-benzyl-4-(4-methoxy-2,3-dimethylbenzyl) piperazine, 1-[(6-nitro-1,3-benzodioxol-5-yl)methyl]-4-phenylpiperazine, 4-[4-nitro-3-(2-phenoxyethoxy)phenyl]morpholine, 1-(3-chlorophenyl)-4-[(6-nitro-1,3-benzodioxol-5-yl)methyl] piperazine, 1-(4-methoxybenzyl)-4-(3-methylbenzyl)piperazine, 4-(4-methoxy-2,3-dimethylbenzyl) morpholine, 1-benzyl-4-(4-methoxy-3-methylbenzyl)piperazine, 1-(4-methoxy-2,3-dimethylbenzyl)-4-methyl piperazine, 1-(4-methoxy-2,3-dimethylbenzyl)-4-methylpiperazine, 1-(1, 3-benzodioxol-5-ylmethyl)-4-(4,5-dimethoxy-2-nitrobenzyl)piperazine, 1-(2,3-dimethylphenyl)-4-(4-methoxy-2,3-dimethylbenzyl)piperazine, 1-(4-methoxy-2,3-dimethylbenzyl)-4-phenylpiperazine, 1-[3-(4-iodophenoxy)propyl]piperidine, 1-(4-methoxy-2,3-dimethylbenzyl)-4-(4-methylphenyl)piperazine, 2-{[(2-methoxy-1-naphthyl)methylene]amino}-1H-isoindole-1,3(2H)-dione, 2-[(2-ethoxybenzylidene)amino]-1H-isoindole-1,3(2H)-dione, 3-ethyl-5-(4-hydroxybenzylidene)-2-thioxo-1,3-thiazolidin-4-one, 3-butyl-5-(3-hydroxybenzylidene)-2-thioxo-1,3-thiazolidin-4-one, 5-(3-bromo-4-methoxybenzylidene)-3-methyl-2-thioxo-1,3-thiazolidin-4-one, 5-(5-bromo-2-hydroxybenzylidene)-3-ethyl-2-thioxo-1,3-thiazolidin-4-one, 2-phenyl-4-(2-thienylmethylene)-1,3-oxazol-5(4H)-one, 5-(4-chlorobenzylidene)-3-(2-methoxyphenyl)-2-thioxo-1,3-thiazolidin-4-one, 3-(4-bromophenyl)-5-(4-hydroxybenzylidene)-2-thioxo-1,3-thiazolidin-4-one, 4-[3-bromo-4-(dimethylamino)benzylidene]-2-(2-methoxyphenyl)-1,3-oxazol-5(4H)-one, 4-[2-(4-nitrophenyl)vinyl]phenol, 3-{2-[(4-fluorobenzyl)amino]phenyl}-2(1H)-quinoxalinone, 4-bromo-3-chlorophenyl)(4-ethoxybenzylidene)amine, 4-[(2-chloro-5-nitrobenzylidene)amino]phenol, 2-[(2-hydroxy-3,5-diiodobenzylidene)amino]-4,6-dimethylphenol, (2-methoxybenzyl)(4-methoxy-3-biphenylyl)amine, 2-{[(5-ethyl-2-hydroxyphenyl)imino]methyl}-4,6-diiodophenol, 3-methoxy-4-(4-nitrophenoxy)benzaldehyde oxime. In some embodiments, a honeybee repellent may be optionally substituted 1-butyl-4-hydroxy-2-oxo-N-(2-pyridinylmethyl)-1,2-dihydro-3-quinolinecarboxamide, 2-acetyl-4-chlorophenyl 4-methylbenzoate, N-(2-fluorobenzyl)-4-hydroxy-2-oxo-1-propyl-1,2-dihydro-3-quinolinecarboxamide, ethyl 2-(benzoylamino)-5-ethyl-3-thiophenecarboxylate, 2-(benzoylamino)-N-(2-chlorophenyl)benzamide, ethyl 2-(3-aminophenyl)-4-quinolinecarboxylate, 1-(4-bromobenzoyl)-2,2,4-trimethyl-1,2-dihydroquinoline, dimethyl 2-(1,2,2-trimethyl-3-thioxo-2,3-dihydro-4(1H)-quinolinylidene)-1,3-dithiole-4,5-dicarboxylate, dimethyl 2-(2,2,7-trimethyl-3-thioxo-2,3-dihydro-4(1H)-quinolinylidene)-1,3-dithiole-4,5-dicarboxylate, N-(4-methoxy-2,3-dimethylbenzyl)-N,N',N'-trimethyl-1,2-ethanediamine, 1,2,3-trichloro-4-(isopropylamino)anthra-9,10-quinone, [1-(3-nitrobenzyl)-3-piperidinyl]methyl 3-phenylacrylate, (3-amino-4,6-dimethylthieno[2,3-b]pyridin-2-yl)(4-chlorophenyl)methanone, (4-bromophenyl)(5-methoxy-2-methyl-1-benzofuran-3-yl)methanone, 1-(4-methoxyphenyl)-3-(2-methyl-1H-indol-3-yl)-2-propen-1-one, or 2-[2-(3,5-dimethyl-1H-pyrazol-1-yl)-6-phenyl-4-pyrimidinyl]phenol, or any combination thereof.

67. A composition comprising a compound according to any one of embodiments 1-66.
68. The composition according to embodiment 67, wherein the composition comprises a two or more different compound according to any one of embodiments 1-66, three or more different compound according to any one of embodiments 1-66, four or more different compound according to any one of embodiments 1-66, or five or more different compound according to any one of embodiments 1-66.
69. The composition according to embodiments 67 and 68, wherein the composition further comprises a solvent, a wetting agent, an emulsifying agent, a carrier, a diluent, or a dispersing agent.
70. The composition according to embodiments 67-69, wherein the composition is a liquid form or a solid form.
71. The composition according to embodiments 67-70, wherein the composition further comprises one or more an adhesive, a solvent, a wetting agent, an emulsifying agent, a carrier, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof.
72. The composition according to embodiment 71, wherein the composition further comprises an insecticide.
73. The composition according to embodiment 72, wherein the insecticide is an organochlorine, an organophosphate, a carbamate, a pyrethroid, or a neonicotinoid.
74. The composition according to embodiment 73, wherein the neonicotinoid is Acetamiprid, Clothianidin, Imidacloprid, Nitenpyram, Nithiazine, Thiacloprid, or Thiamethoxam.
75. A use of a honeybee repellent according to any one of embodiments 1-66 or a composition according to any one of embodiments 67-74 to repel a honeybee from a location by applying the compound or the composition to the location.
76. A use of a honeybee repellent according to any one embodiments 1-66 or a composition according to any one of embodiments 67-74 to repel a honeybee from foraging and/or collecting nectar from a flower of a plant by applying the compound or the composition to the plant or in a location in the vicinity of the plant.
77. A use of a honeybee repellent according to any one of embodiments 1-66 or a composition according to any one of embodiments 67-74 to repel a honeybee from a structure by applying the compound or the composition to the structure or in a location in the vicinity of the structure.
78. A method of repelling a honeybee from a location, the method comprising the step of applying a honeybee repellent according to any one of embodiments 1-66 or a composition according to any one of embodiments 67-74 to a location, wherein application of the compound or the composition to the location repels a honeybee from the location.
79. A method of repelling a honeybee from a plant, the method comprising the step of applying a honeybee repellent according to any one of embodiments 1-66 or a composition according to any one of embodiments 67-74 to a plant or in a location in the vicinity of the plant, wherein application of the compound or the composition to the location repels a honeybee from foraging and/or collecting nectar from a flower of the treated plant.
80. A method of repelling a honeybee from a structure, the method comprising the step of applying a honeybee repellent according to any one of embodiments 1-66 or a composition according to any one of embodiments 67-74 to a structure or in a location in the vicinity of the structure, wherein application of the compound or the composition to the structure repels a honeybee from the structure.
81. A seed composition comprising a seed and a honeybee repellent according to any one of embodiments 1-66 or a composition according to any one of embodiments 67-74.
82. A seed composition of embodiment 81, wherein the composition further comprises one or more of an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, a larvicide, a seed, or any combination thereof 83. A device comprising a honeybee repellent according to any one of embodiments 1-66 or a composition according to any one of embodiments 67-74.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, compositions, pharmaceutical kits, methods or uses of repelling honeybees.

Example 1

Testing of Candidate Compounds Using Binding Assay

To identify a honeybee repellent disclosed herein, candidate compounds were screened based upon the fact that 2-heptanone is an established repellent of bees. 2-heptanone is thought to mediate its behavioral response through binding to a specific odorant-binding protein called OBP2. Therefore compounds that bind OBP2 have the potential to act as odor "mimics" of 2-heptanone. By utilizing a fluorescent-quench, ligand-protein-binding assay, 30,000 compounds from the DIVERSET® library (ChemBridge Corp., San Diego, Calif.), a chemical library, were screened and over 150 candidate compounds were isolated that bind OBP2 (Table 1). Such assays are generally known in the art. See, e.g., Briand, et al., Ligand-Binding Properties and Structural Characterization of a Novel Rat Odorant-Binding Protein Variant, Eur. J. Biochem. 267(10): 3079-3089 (2000); Briand, et al., Ligand Binding and Physico-Chemical Properties of ASP2, A Recombinant Odorant-Binding Protein From Honeybee (*Apis mellifera* L.), Eur. J. Biochem. 268(3): 752-760 (2001); Briand, et al., Characterization of a Chemosensory Protein (ASP3c) from Honeybee (*Apis mellifera* L.) as a Brood Pheromone Carrier, Eur. J. Biochem. 269(18): 4586-4596 (2002), each of which is hereby incorporated by reference in its entirety.

Example 2

Testing of Candidate Compounds Using the PER Assay

To determine whether a living honeybee can recognize a candidate compound, these compounds were tested using a proboscis extension response (PER) assay using classical conditioning approaches. Proboscis extension response conditioning is a case of appetitive learning, in which bees learn to associate odor stimuli with sucrose reward in the laboratory. In this case, bees were conditioned to produce a PER to 2-heptanone as the conditioned stimulus and a sugar reward as the unconditioned stimulus. These trained bees were then exposed to an odor pulse of a candidate compound to test whether a candidate compound would also produce a PER. If the candidate compound "mimics" 2-heptanone then the honeybee will extend its proboscis.

For conditioning procedures, *Apis mellifera* Carniolan foraging worker honeybees were obtained from a local apiary (typically 60 bees per shipment). The honeybees were held overnight in insect cages with food and water freely available, in an environmentally controlled room on a light cycle similar to the ambient cycle at the time of the assay.

For conditioning procedures, all tests were done in an odorant delivery apparatus set inside a fume hood. The apparatus comprised a set of open-ended, horizontal, 3 cm diameter by 10 cm long plastic tubes. Each tube was designed where a honeybee could be positioned at the distal end of a tube, with the opening at the other end of the tube located proximal to an inlet of the fume hood. To deliver an odorant, room air was pumped by a diaphragm pump through a particle filter via 0.25 inch plastic tubing at approximately 0.7 m/sec. The air flow passes into the headspace above an odorant (0.5% [v/v]2-heptanone dissolved in odorless light paraffin oil) contained in a 100 mL bottle. The headspace air then passes through another plastic tube to a manifold of 4-way valves, each of which was attached near the proximal end of a plastic tube containing a bee. Each bee was exposed separately for a desired time period to the odorant by opening and closing the appropriate valve. When each valve was closed, the odor was flushed away immediately by the continuous fume hood air stream.

To train a honeybee to respond to a conditioned and unconditioned stimuli, bees were placed, without anesthesia, in individual 1.5 mL micro-centrifuge holding tubes and held overnight without access to food or water. The holding tubes containing the starved bees were placed in racks in groups of eight. One rack at a time was placed behind the odorant delivery apparatus so that each bee's head is centered at the distal end of a horizontal plastic tube. Each bee was exposed to the 2-heptanone odorant alone for four seconds, and then while being fed an 80% sucrose solution for and additional three seconds. The sucrose solution was delivered on a piece of saturated filter paper held in forceps. The wet paper was touched to the bee's antennae if the bee did not immediately extend its proboscis (which usually happens in a fraction of a second after the sucrose solution comes near the bee's head). Positive and negative responses were recorded. A positive PER was scored when a bee extended its proboscis before the sucrose appeared. In a typical trial, 48 individual bees were subjected to conditioning. Six rounds of training were done before testing began, and typically a majority of the bees were successfully conditioned by the second or third round of training.

After conditioning, honeybees were tested with the candidate compounds the same day or on the following day or, most commonly, both. When held overnight, bees were fed with sucrose and kept in their holding tubes. When tested the day after training, bees were given one or more rounds of conditioning with 2-heptatone to refresh their memories. Candidate compounds stocks were made at 5% (w/v) in polyoxyethylene octyl phenyl ether (TRITON® X-100), a non-ionic detergent/surfactant, and stored at 4° C. This detergent is similar to substances used as carriers for a variety of commercial pest-control agents, can act as a solvent for both hydrophilic and hydrophobic substances, and is itself nearly odorless. Test solutions were made fresh daily by mixing stock solutions with water for a final compound concentration of 0.5%. A solution of 0.5% 2-heptanone in paraffin oil was used as a positive control. Both water and 15% polyoxyethylene octyl phenyl ether (TRITON® X-100) in water served as negative controls to eliminate false positives.

For candidate compound testing experiments, a single 3 cm length of 3 cm diameter plastic tube is positioned horizontally in a holder so that air is drawn through it at about 0.7 m/sec. Holding tubes containing a trained honeybee were positioned in racks as for the conditioning procedure. The rack was then moved sequentially behind the tube so that each bee's head was directly behind the rear end of tube for the test. The test compounds and controls were presented on a saturated piece of filter paper held at the front end of the 3 cm tube. Bees in each rack were exposed sequentially to a given candidate compound or control for four seconds and the results recorded. After bees were tested with one compound, the process was repeated for the next candidate compound using a clean tube and testing implements. The order of testing was randomized for each day's test and generally 5-6 different candidate compounds were tested in a single day along with 3 controls. Only bees giving a PER with 2-heptanone, but not with the negative controls were counted in calculating the percent of bees testing positive to each compound (Table 2). Generally about half of the total bees subjected to conditioning exhibited a PER with the 2-heptanone positive control, and only a very small number of these respond to the negative controls. If a given cohort of bees were tested for two consecutive days, they were tested with two separate sets of candidate compounds to maximize the number of individual bees tested with each compound. In a few cases where a single cohort of bees was tested twice with the same compounds. In this case, the results were averaged and the average was used in the calculation of the percent of positives. Table 2 shows the results from the PER assay for 66 candidate compounds. Compounds are ranked in order of the percent 2-heptanone-positive honeybees that were positive to the test compound and negative to both water and 15% polyoxyethylene octyl phenyl ether (TRITON® X-100) controls.

TABLE 2

OBP2 Binding and Proboscis Extension Response (PER) Assay

| No. | Candidate Compound Name | 2-heptanone positive bees (N) | 2-heptanone positive bees testing positive to compound | OBP2 binding characteristic of compound |
|---|---|---|---|---|
| 7 | 1-benzyl-4-(4-methoxy-2,3-dimethylbenzyl)piperazine | 57 | 39.0% | Moderate |
| 40 | 2-acetyl-4-chlorophenyl 4-methylbenzoate | 54 | 34.3% | Moderate |
| 2 | 4-[2-(4-nitrophenyl)vinyl]phenol | 47 | 31.5% | Moderate |
| 1 | 1-(4-methoxyphenyl)-3-(2-methyl-1H-indol-3-yl)-2-propen-1-one | 25 | 26.6% | Moderate |
| 60 | N-[2-(4-chlorophenoxy)ethyl]-5-(3-methyl-1-piperazinyl)-2-nitroaniline | 12 | 25.0% | Moderate |
| 36 | 4-bromo-N'-[2-(trifluoroacetyl)-1-cyclopenten-1-yl]benzohydrazide | 56 | 24.3% | Moderate |
| 50 | 1-(4-methoxyphenyl)-3-(1-methyl-1H-indol-3-yl)-2-propen-1-one | 54 | 22.2% | ND* |
| 48 | N-methyl-N-[(6-nitro-1,3-benzodioxol-5-yl)methyl]-2-(2-pyridinyl)ethanamine | 82 | 18.9% | ND* |
| 47 | 4-[(6-nitro-1,3-benzodioxol-5-yl)methyl]thiomorpholine | 82 | 18.3% | ND* |
| 53 | 6-(4-iodophenyl)imidazo[2,1-b][1,3]thiazole | 11 | 18.2% | Moderate |
| 56 | 4-{[(9-ethyl-9H-carbazol-3-yl)methylene]amino}benzamide | 11 | 18.2% | Moderate |
| 61 | 1-[(6-nitro-1,3-benzodioxol-5-yl)methyl]-4-phenylpiperazine | 35 | 17.4% | Moderate |
| 57 | N-phenyl-N'-[2-(phenylethynyl)phenyl]urea | 12 | 16.7% | Moderate |
| 59 | methyl 3-[(4-fluorobenzoyl)amino]-2-butenoate | 12 | 16.7% | Moderate |
| 51 | 1,1'-(1,4-phenylene)bis[3-(1H-indol-3-yl)-2-propen-1-one] | 54 | 14.8% | ND* |
| 26 | 1-[(6-nitro-1,3-benzodioxol-5-yl)methyl]-4-phenylpiperazine | 61 | 14.8% | ND* |
| 3 | 3-methoxy-4-(4-nitrophenoxy)benzaldehyde oxime | 35 | 14.5% | ND |
| 8 | (3-amino-4,6-dimethylthieno[2,3-b]pyridin-2-yl)(4-chlorophenyl)methanone | 47 | 14.4% | Moderate |
| 37 | 2,2,4-trimethyl-1,2-dihydro-6-quinolinyl 3-methoxybenzoate | 56 | 14.4% | Moderate |
| 52 | 1-(4-biphenylyl)-3-(1H-indol-3-yl)-2-propen-1-one | 54 | 13.9% | ND* |
| 55 | N'-(4-bromo-5-methyl-2-oxo-1,2-dihydro-3H-indol-3-ylidene)spiro[2.3]hexane-1-carbohydrazide | 11 | 13.6% | Moderate |
| 46 | 1-(1,3-benzodioxol-5-ylmethyl)-4-(4,5-dimethoxy-2-nitrobenzyl)piperazine | 82 | 12.8% | ND* |
| 45 | 1-methyl-4-[(6-nitro-1,3-benzodioxol-5-yl)methyl]piperazine | 82 | 11.6% | ND* |
| 62 | 1-(4-methoxy-2,3-dimethylbenzyl)-4-methylpiperazine | 35 | 11.6% | ND |
| 63 | 4-(4-methoxy-2,3-dimethylbenzyl)morpholine | 32 | 10.9% | ND |

TABLE 2-continued

OBP2 Binding and Proboscis Extension Response (PER) Assay

| No. | Candidate Compound Name | 2-heptanone positive bees (N) | 2-heptanone positive bees testing positive to compound | OBP2 binding characteristic of compound |
|---|---|---|---|---|
| 9 | 2-phenyl-4-(2-thienylmethylene)-1,3-oxazol-5(4H)-one | 52 | 9.7% | Moderate |
| 54 | 2-(3-bromophenyl)-2-oxoethyl benzoate | 11 | 9.1% | Moderate |
| 35 | 4-hydroxy-3-[2-(4-hydroxyphenyl)-2,3-dihydro-1,5-benzothiazepin-4-yl]-6-methyl-2H-pyran-2-one | 56 | 9.0% | Moderate |
| 13 | 2-{[(2-methoxy-1-naphthyl)methylene]amino}-1H-isoindole-1,3(2H)-dione | 52 | 8.7% | ND |
| 33 | 4-(4-methoxy-2,3-dimethylbenzyl)morpholine | 41 | 8.5% | Low* |
| 58 | 3-[(4-chlorobenzoyl)amino]propyl 4-chlorobenzoate | 12 | 8.3% | Moderate |
| 44 | methyl 5-{[(4-bromophenyl)amino]sulfonyl}-2-chlorobenzoate | 76 | 7.3% | Moderate |
| 5 | 5-(4-chlorobenzylidene)-3-(2-methoxyphenyl)-2-thioxo-1,3-thiazolidin-4-one | 43 | 7.1% | ND |
| 64 | 1-(3-chlorophenyl)-4-[(6-nitro-1,3-benzodioxol-5-yl)methyl]piperazine | 58 | 7.0% | Moderate |
| 20 | 2-[2-(3,5-dimethyl-1H-pyrazol-1-yl)-6-phenyl-4-pyrimidinyl]phenol | 45 | 6.7% | Strong |
| 43 | 5-(1,3-benzodioxol-5-ylmethylene)-3-(1,5-dimethyl-3-oxo-2-phenyl-2,3-dehydro-1H-pyrazol-4-yl)-2-thioxo-1,3-thiazolidin-4-one | 76 | 6.6% | Moderate |
| 25 | 1-(4-methoxy-2,3-dimethylbenzyl)-4-methylpiperazine | 61 | 6.6% | Low* |
| 65 | 1-(4-methoxybenzyl)-4-(3-methylbenzyl)piperazine | 32 | 6.3% | ND |
| 16 | 1-butyl-4-hydroxy-2-oxo-N-(2-pyridinylmethyl)-1,2-dihydro-3-quinolinecarboxamide | 73 | 6.2% | Strong |
| 17 | (4-bromophenyl)(5-methoxy-2-methyl-1-benzofuran-3-yl)methanone | 73 | 6.2% | Strong |
| 12 | (4-bromo-3-chlorophenyl)(4-ethoxybenzylidene)amine | 52 | 5.8% | ND |
| 27 | 1-benzyl-4-(4-methoxy-3-methylbenzyl)piperazine | 35 | 5.8% | Low* |
| 34 | 1-(4-methoxybenzyl)-4-(3-methylbenzyl)piperazine | 41 | 4.9% | ND* |
| 38 | N'-[(2-chlorobenzoyl)oxy]benzenecarboximidamide | 41 | 4.9% | Moderate |
| 10 | 2-(benzoylamino)-N-(2-chlorophenyl)benzamide | 52 | 4.8% | Moderate |
| 11 | 1-(4-bromobenzoyl)-2,2,4-trimethyl-1,2-dihydroquinoline | 52 | 4.8% | Moderate |
| 24 | 1-(3-chlorophenyl)-4-[(6-nitro-1,3-benzodioxol-5-yl)methyl]piperazine | 84 | 4.8% | ND |
| 4 | dimethyl 2-(1,2,2-trimethyl-3-thioxo-2,3-dihydro-4(1H)-quinolinylidene)-1,3-dithiole-4,5-dicarboxylate | 43 | 4.7% | ND |
| 21 | ethyl 2-(3-aminophenyl)-4-quinolinecarboxylate | 45 | 4.4% | Strong |
| 22 | 1,2,3-trichloro-4-(isopropylamino)anthra-9,10-quinone | 45 | 4.4% | Strong |
| 15 | 3-ethyl-5-(4-hydroxybenzylidene)-2-thioxo-1,3-thiazolidin-4-one | 73 | 4.1% | Strong |
| 18 | 3-{2-[(4-fluorobenzyl)amino]phenyl}-2(1H)-quinoxalinone | 73 | 4.1% | Strong |
| 14 | 4-[4-nitro-3-(2-phenoxyethoxy)phenyl]morpholine | 52 | 3.9% | Moderate |
| 23 | [1-(3-nitrobenzyl)-3-piperidinyl]methyl 3-phenylacrylate | 45 | 3.3% | Strong |
| 66 | N-(4-methoxy-2,3-dimethylbenzyl)-N,N',N'-trimethyl-1,2-ethanediamine | 32 | 3.1% | ND |
| 19 | dimethyl 2-(2,2,7-trimethyl-3-thioxo-2,3-dihydro-4(1H)-quinolinylidene)-1,3-dithiole-4,5-dicarboxylate | 73 | 2.8% | Strong |
| 42 | 2,6-di-tert-butylbenzo-1,4-quinone 4-thiosemicarbazone | 76 | 2.6% | Moderate |

TABLE 2-continued

OBP2 Binding and Proboscis Extension Response (PER) Assay

| | Candidate Compound | 2-heptanone positive bees (N) | 2-heptanone positive bees testing positive to compound | OBP2 binding characteristic of compound |
|---|---|---|---|---|
| No. | Name | | | |
| 32 | N-(4-methoxy-2,3-dimethylbenzyl)-N,N',N'-trimethyl-1,2-ethanediamine | 41 | 2.4% | ND* |
| 39 | N-benzyl-2-phenyl-N-(3-pyridinylmethyl)ethanamine | 54 | 1.9% | Moderate |
| 41 | ethyl methyl 4-(4-bromophenyl)-2,6-dimethyl-1,4-dihydro-3,5-pyridinedicarboxylate | 72 | 1.4% | Moderate |
| 6 | 7-(diethylamino)-4-methyl-3-nitro-2H-chromen-2-one | 43 | 0.0 | ND |
| 28 | 1-(4-methoxy-2,3-dimethylbenzyl)-4-(3-phenyl-2-propen-1-yl)piperazine | 35 | 0.0 | Low* |
| 29 | 1-(2,3-dimethylphenyl)-4-(4-methoxy-2,3-dimethylbenzyl)piperazine | 35 | 0.0 | Low* |
| 30 | 1-(4-methoxy-2,3-dimethylbenzyl)-4-phenylpiperazine | 35 | 0.0 | ND* |
| 31 | 2-[4-(4-methoxy-2,5-dimethylbenzyl)-1-piperazinyl]ethanol | 35 | 0.0 | ND* |
| 49 | 1-(4-methoxy-2,3-dimethylbenzyl)-4-(4-methylphenyl)piperazine | 54 | 0.0 | ND* |

ND, not determined.
Low, indicates no detectable binding to OBP2.
Moderate, indicates that 50% or less of the compound bound to OBP2.
Strong, indicates that 51% or more of the compound bound to OBP2.
*Compound selected by in silico analysis.

Example 3

Testing of Candidate Compounds Using Choice Test

To determine whether living honeybees will choice to move towards a source of a candidate compound, these compounds were assayed using a choice test in a free-flight box apparatus.

All tests were done in a free-flight box apparatus. The apparatus comprises a 244 cm long×46 cm deep×30 cm high clear plastic box including two equally-sized independent testing chambers, each with 10 cm diameter air inlets that admit filtered room air, separated by a smaller central chamber with a screened air outlet to each testing chamber. Air can be pulled through the sealed box via a 10 cm diameter duct from the air outlet using an AQE Fume Fighter 500 fume extractor (BPA Air Quality Solutions, LLC, Charleston, S.C.), which removes the test odors using activated charcoal and HEPA filters. The box is housed in an environmentally controlled room with overhead illumination timed to correspond to the current ambient light cycle including 2 additional sets of lights timed to approximate crepuscular lighting conditions. The bottom of the apparatus was lined with clean absorbent paper marked with a 4×9 grid pattern, forming 12 cm×12 cm squares with marked coordinates.

Apis mellifera Carniolan foraging worker honeybees were obtained from a local apiary (typically 60 bees per shipment). Thirty honeybees were put into each testing chamber and were allowed to acclimate for 24 hours with food and water freely available.

At the beginning of each test day all food was removed from the test chamber, but water was continually available throughout all tests. For each test, approximately 0.3 g of organic, raw orange blossom honey was added to each clean small plastic weigh boat (Cole-Palmer). The honey boats were placed in small plastic culture dishes, which were distributed in the marked squares in the chambers. The positions of the dishes on the grid for a set of trials was chosen to avoid the bees' preferred resting area so that they had to find the food actively, but the same dish positions were maintained for a given set of trials. We used seven dishes of honey: six to which the bees had access and a seventh that had a screened lid. The honey in each boat was weighed on an analytical balance before and after the test, with the screened sample as a control for evaporative loss. The fume extractor was left off during the experimental trails, and was turned on to clear the air after the test dishes were covered and removed from the chamber at the end of each trial.

Based on the observation that bees tend to return to dishes in the same position where they have fed before, each set of trials with each group of bees began with "Pattern Identification" tests to see which dishes lose the most weight, reflecting the most feeding. Once bees were consuming an acceptable amount in 10-15 min, typically in 1-2 trials, we began a set of test compound trials. The test compound was pipetted onto pieces of filter paper placed on the dish bottom below the boat containing a fresh, weighed honey sample so that the test compound was inaccessible to the bees. We used 2 µL of a candidate compound at a concentration of 0.05-0.5%, in Triton X-100 or paraffin oil, on each of four pieces of filter paper per dish. The test-solution dishes were set at the same positions as the one or two dishes favored in the preceding Pattern Identification trial. To eliminate interference from the solvent, the other dishes without the test substance contained the same volume of the appropriate solvent on filter papers as the test solution dishes. The bees were allowed to feed for 10-15 minutes. Bee movements were recorded by a small, wide-angle digital video camcorder (HD Hero 960; GoPro, Halfmoon Bay, Calif.) placed on a tripod in front of the test chamber. The bees were given a brief rest while the honey was weighed and a second test was begun with fresh dishes, except that the test compound-containing dish or dishes were placed at whichever positions were most visited in the preceding test. Tests were continued until the bees' feeding slowed significantly, typically in 2-4 trials. The bees were then rested for 1-3 hours and a subsequent set of trials begun with another Pattern Identification. Tests were performed in both chambers simultaneously, with the same test compounds. Groups of bees can perform as many as nine tests in one day, with an average of about seven on the first day and somewhat fewer on subsequent days, usually for three days.

The results of the free-flight choice tests are shown in Table 3. To validate the test system, the known honeybee repellent, 2-heptanone, at the concentration used in the PER assays was used as a positive control for repellency. In addition, neroli oil, a component of commercial honeybee attractants (swarm lures), was used as a positive control for an attractant. Lastly, a dish containing food alone was used as a control for the components in the solution minus the candidate compound. Candidate compounds with high PER scores as well as compounds with lower PER scores to examined in order to correlated the results from the choice test. Using the criterion of reduction of feeding at dishes that were most visited in the preceding test, candidate compounds with high PER scores attracted honeybees as well as, or better, than 2-heptanone as repellents (Table 3), while weaker performers in the PER assay were generally less effective repellents. The attractant effect of neroli oil was also detectable, and one of the weak PER compounds (No. 8) actually scored as slightly attractive (Table 3). Two of the candidate compounds (Nos. 2 and 26) were significantly more effective when tested at a 10-fold lower concentration (Table 3).

TABLE 3

Choice Tests In Free-Flight Box Apparatus

| No. | Candidate Compound Name | Amount | % Positive in PER | Number trials/bee groups | Repellence Score[1] | Quintile Rank Change Score[2] |
|---|---|---|---|---|---|---|
| — | 2-heptanone | 0.5% | — | 56/12 | 54.6% | −2.73 |
| — | Neroli oil | 0.5% | — | 16/3 | −65% | 3.88 |
| — | No compound | 0 | — | 1937/46 | — | −0.31 |
| 7 | 1-benzyl-4-(4-methoxy-2,3-dimethylbenzyl)piperazine | 0.1% | 39.0 | 30/8 | 62.0% | −3.10 |
| 2 | 4-[2-(4-nitrophenyl)vinyl]phenol | 0.5% | 31.5 | 33/8 | 37.6% | −1.88 |
|  |  | 0.05% | ND | 17/5 | 57.7% | −2.88 |
| 40 | 2-acetyl-4-chlorophenyl 4-methylbenzoate | 0.5% | 30.5 | 19/8 | 54.6% | −2.25 |
| 1 | 1-(4-methoxyphenyl)-3-(2-methyl-1H-indol-3-yl)-2-propen-1-one | 0.5% | 26.6 | 42/12 | 57.8% | −2.89 |
| 36 | 4-bromo-N'-[2-(trifluoroacetyl)-1-cyclopenten-1-yl]benzohydrazide | 0.5% | 24.3 | 15/7 | 56.3% | −2.65 |
| 50 | 1-(4-methoxyphenyl)-3-(1-methyl-1H-indol-3-yl)-2-propen-1-one | 0.5% | 22.2 | 4/2 | 55.7% | −2.33 |
| 26 | 1-[(6-nitro-1,3-benzodioxol-5-yl)methyl]-4-phenylpiperazine | 0.5% | 14.8 | 30/7 | 58.6% | −2.93 |
|  |  | 0.05% | ND | 26/7 | 60.0% | −3.00 |
| 3 | 3-methoxy-4-(4-nitrophenoxy)benzaldehyde oxime | 0.5% | 14.5 | 23/11 | 49.8% | −1.4 |
| 8 | (3-amino-4,6-dimethylthieno[2,3-b]pyridin-2-yl)(4-chlorophenyl)methanone | 0.5% | 14.4 | 6/3 | −10.7% | 1.05 |
| 9 | 2-phenyl-4-(2-thienylmethylene)-1,3-oxazol-5(4H)-one | 0.5% | 9.7 | 15/6 | 43.3% | −1.13 |
| 10 | 2-(benzoylamino)-N-(2-chlorophenyl)benzamide | 0.5% | 4.8 | 25/6 | 45.6% | −1.28 |

[1]Repellence Score is the percent food-weight change in dishes containing the test molecule, compared to corresponding dishes in the preceding test, averaged over all of the tests (a negative score = an increase in food consumption).
[2]Quintile Rank Change Score is calculated by ranking the weight of food eaten in each dish as a percent of total food in all dishes in quintiles (1 = most food eaten), then subtracting the rank of each dish containing the test compound in one test run from the rank of the corresponding dish in the preceding test and averaging over all of the tests. A negative score indicates a decrease in food eaten; a positive score indicates an increase in food eaten.
ND, not determined.

Example 4

Use of Honeybee Repellent in Conjunction with Insecticide

This example illustrates how to use a honeybee repellent disclosed herein to repel honeybees from an area where insecticides have also been applied in order to reduce honeybee mortality and avoid insecticide contamination of honey, beeswax, and other hive products.

At the start of a growing season, an almond tree grower delays the use of a nicotine-based insecticide like Clothianidin and Imidacloprid in order to minimize harmful effects of this insecticide on honeybees while these insects enter his almond tree orchards. While gathering nectar from the flowers of the almond trees, the honeybees pollinate the trees. Subsequently the grower does apply a nicotine-based insecticide like Clothianidin and Imidacloprid to his orchards. At the same or similar time, the grower also applies a honeybee repellent disclosed herein. The grower may periodically applies the repellant using the same schedule as that for the insecticide, or one based on the half-life of the honeybee repellent. The grower realizes typical yields of almonds, while at the same time his neighbor, who is a

Example 5

Use of Honeybee Repellent to Increase Yields of Seedless Crops

This example illustrates how to use a honeybee repellent disclosed herein to prevent unwanted pollination of crop plants by honeybees where such pollination reduces the market value due to the resulting seeded crop.

At the start of a growing season, a mandarin orange grower applies a nicotine-based insecticide like Clothianidin and Imidacloprid. At the same or similar time, the grower also applies a honeybee repellent disclosed herein. The grower may periodically applies the repellant using the same schedule as that for the insecticide, or one based on the half-life of the honeybee repellent. The grower realizes excellent yields of seedless mandarin oranges. A beekeeper nearby reports that his bee colonies are healthy.

Example 6

Use of Honeybee Repellent to Increase Yields of Seedless Crops

This example illustrates how to use a honeybee repellent disclosed herein to prevent unwanted pollination of crop plants by honeybees where such pollination reduces the market value due to the resulting seeded crop.

At the start of a growing season, a tangerine grower applies a honeybee repellent disclosed herein. The grower may periodically apply the repellant based on its half-life. The grower realizes excellent yields of seedless tangerine. A beekeeper nearby reports that his bee colonies are healthy.

Example 7

Use of Honeybee Repellent to Control Honeybee Presence in Outdoor Area

This example illustrates how to use a honeybee repellent disclosed herein to keep away honeybees from outdoor areas where human activities are occurring and would be disrupted by honeybee presence, such as, e.g., an outdoor activity like a sporting event or picnic.

At the start of a Fourth of July picnic, a mother applies a honeybee repellent disclosed herein in the area where her family is setting up table and grill. The mother realizes that, unlike previous events of this nature, honeybees did not seem to bother her family while they were eating their lunch.

Example 8

Use of Honeybee Repellent to Control Honeybee Presence in Structure

This example illustrates how to use a honeybee repellent disclosed herein to keep away honeybees from man-made structures in order to prevent infestation of a colony, such as, e.g., a commercial building, a house, a shed, or other structure.

A man recently had an exterminator remove a bee colony that established a hive inside one of the ways of his house. This was a reoccurring problem as it had happened three previous two years as well. After removal, the exterminator applied a honeybee repellent disclosed herein and also explained to the homeowner that he should periodically apply the repellent in order to prevent a further infestation. The homeowner did as instructed. The next year honeybees did not establish a hive in the man's house.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of repelling a honeybee from a location or a structure or a plant, the method comprising the step of applying a honeybee repellent to the location, the structure, the plant and/or in a vicinity nearby the location, the structure, or the plant, wherein application of the honeybee repellent to the location, the structure or the plant repels a honeybee from the location, the structure, or the plant, wherein the honeybee repellent has a structure of formula XIIIa:

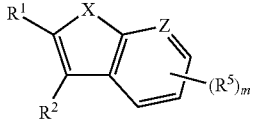

XIIIa wherein X is C, N, O or S; Z is C or N; $R^1$ is selected from H, OH, $C_{1-6}$ alkyl, $OC_{1-6}$ alkyl, $CO_2C_{1-6}$ alkyl, halogen, $NO_2$, or $SO_2$; and $R^2$ is selected from $C_{1-6}$ alkyl, $C_{2-6}$ alkenyl, $C_{2-6}$ alkynyl, $C_{1-6}$ cycloalkyl, $C_{2-6}$ cycloalkenyl, $C_{2-6}$ cycloalkynyl, optionally substituted alkylaryl, optionally substituted arylalkyl, alkoxy, optionally substituted aryloxy, optionally substituted arylalkoxy, optionally substituted alkoxyalkylaryl, heteroalkyl, optionally substituted heteroaryl, optionally substituted heteroarylalkyl, cyclic heteroalkyl, cyclic heteroalkylalkyl, acyl, optionally substituted benzoyl, optionally substituted 2-benzoylethenyl, OH, $OR^5$, CN, $OCF_3$, $CF_3$, Br, Cl, F, alkylcarbonyl, morpholino, piperidinyl, dioxanyl, pyranyl, optionally substituted heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline; $R^5$ is each independently H, OH, $C_{1-6}$ alkyl, $OC_{1-6}$ alkyl, $OC_{1-6}$ cycloalkyl, $CO_2C_{1-6}$ alkyl, $CO_2C_{1-6}$ cycloalkyl, halogen, $NO_2$, or $SO_2$; and m is 0 to 5.

2. The method of claim 1, wherein the honeybee repellent has a structure of formula XIIIa:

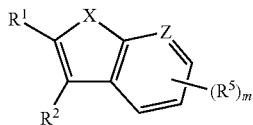

XIIIa wherein X is N, O or S; Z is C; $R^1$ is selected from OH, $C_{1-6}$ alkyl, $OC_{1-6}$ alkyl, $CO_2C_{1-6}$ alkyl, halogen, $NO_2$, or $SO_2$; $R^2$ is selected from $C_{1-6}$ alkyl, $C_{2-6}$ alkenyl, $C_{2-6}$ alkynyl, $C_{1-6}$ cycloalkyl, $C_{2-6}$ cycloalkenyl, $C_{2-6}$ cycloalkynyl, optionally substituted alkylaryl, optionally substituted arylalkyl, alkoxy, optionally substituted aryloxy, optionally substituted arylalkoxy, optionally substituted alkoxyalkylaryl, acyl, optionally substituted benzoyl, optionally substituted 2-benzoylethenyl, OH, $OR^5$, CN, $OCF_3$, $CF_3$, Br, Cl, F, alkylcarbonyl, morpholino, piperidinyl, dioxanyl, pyranyl, optionally substituted heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline; $R^5$ is each independently H, OH, $C_{1-6}$ alkyl, $OC_{1-6}$ alkyl, $OC_{1-6}$ cycloalkyl, halogen; and m is 0 to 2.

3. The method of claim 1, wherein the honeybee repellent is an optionally substituted 1-(4-methoxyphenyl)-3-(2-methyl-1H-indol-3-yl)-2-propen-1-one (Compound 1), an optionally substituted 1-(4-methoxyphenyl)-3-(1-methyl-1H-indol-3-yl)-2-propen-1-one (Compound 50), an optionally substituted (4-bromophenyl)(5-methoxy-2-methyl-1-benzofuran-3-yl)methanone (Compound 17) or any combination thereof.

4. The method of claim 3, wherein the honeybee repellent is 1-(4-methoxyphenyl)-3-(2-methyl-1H-indol-3-yl)-2-propen-1-one, 1-(4-methoxyphenyl)-3-(1-methyl-1H-indol-3-yl)-2-propen-1-one, (4-bromophenyl)(5-methoxy-2-methyl-1-benzofuran-3-yl)methanone or any combination thereof.

5. The method of claim 3, wherein the honeybee repellent has a structure according to any one of the following formulae:

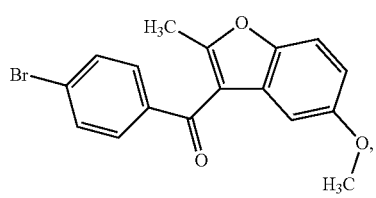

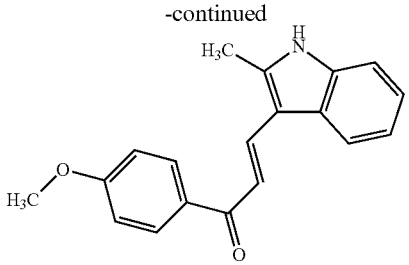

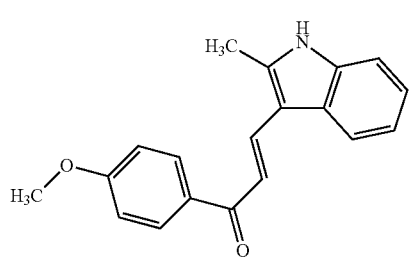 or

6. The method of claim 1, wherein the repelling a honeybee from a location or a structure or a plant prevents the honeybee from foraging and/or collecting nectar.

7. The method of claim 1, wherein application of the honeybee repellent to the location, the structure, the plant and/or in the vicinity nearby the location, the structure, or the plant is achieved using a seed composition that is coated with the honeybee repellent.

8. The method of claim 1, wherein application of the honeybee repellent to the location, the structure, the plant and/or in the vicinity nearby the location, the structure, or the plant is achieved using a device comprising the honeybee repellent.

* * * * *